US008968715B2

(12) United States Patent
Chowdhary et al.

(10) Patent No.: US 8,968,715 B2
(45) Date of Patent: *Mar. 3, 2015

(54) DRUG DELIVERY SYSTEMS FOR PHOTODYNAMIC THERAPY

(75) Inventors: Rubinah K. Chowdhary, Vancouver (CA); David Dolphin, Vancouver (CA)

(73) Assignee: The University of British Columbia, Vancouver (CA)

(*) Notice: Subject to any disclaimer, the term of this patent is extended or adjusted under 35 U.S.C. 154(b) by 1791 days.

This patent is subject to a terminal disclaimer.

(21) Appl. No.: 11/601,559

(22) Filed: Nov. 17, 2006

(65) Prior Publication Data

US 2007/0086973 A1    Apr. 19, 2007

Related U.S. Application Data

(63) Continuation of application No. 10/688,090, filed on Oct. 17, 2003, now abandoned, which is a continuation of application No. 09/851,641, filed on May 8, 2001, now Pat. No. 6,693,093.

(60) Provisional application No. 60/202,641, filed on May 8, 2000.

(51) Int. Cl.
| | | |
|---|---|---|
| *A61K 31/00* | (2006.01) | |
| *A61K 9/14* | (2006.01) | |
| *A61K 31/555* | (2006.01) | |
| *A61K 31/40* | (2006.01) | |
| *A61K 9/00* | (2006.01) | |
| *A61K 9/10* | (2006.01) | |
| *A61K 9/127* | (2006.01) | |
| *A61K 31/409* | (2006.01) | |
| *A61K 31/787* | (2006.01) | |
| *A61K 41/00* | (2006.01) | |

(52) U.S. Cl.
CPC .............. *A61K 9/0009* (2013.01); *A61K 9/0019* (2013.01); *A61K 9/10* (2013.01); *A61K 9/1278* (2013.01); *A61K 31/409* (2013.01); *A61K 31/555* (2013.01); *A61K 31/787* (2013.01); *A61K 41/00* (2013.01); *A61K 41/0057* (2013.01); *A61K 41/0071* (2013.01)
USPC ........... 424/78.3; 424/486; 514/185; 514/410

(58) Field of Classification Search
USPC .......................... 424/78.3, 486; 514/185, 410
See application file for complete search history.

(56) References Cited

U.S. PATENT DOCUMENTS

| | | | |
|---|---|---|---|
| 4,511,641 A * | 4/1985 | Busman et al. ................ 430/158 |
| 5,171,749 A | 12/1992 | Levy et al. | |
| 5,173,504 A | 12/1992 | Dougherty | |
| 5,308,608 A | 5/1994 | Dolphin et al. | |
| 5,405,957 A | 4/1995 | Tang et al. | |
| 5,512,675 A | 4/1996 | Tang et al. | |
| 5,616,342 A | 4/1997 | Lyons | |
| 5,703,230 A | 12/1997 | Boyle et al. | |
| 5,726,304 A | 3/1998 | Tang et al. | |
| 5,831,088 A | 11/1998 | Dolphin et al. | |
| 5,880,145 A | 3/1999 | Sternberg et al. | |
| 5,883,246 A | 3/1999 | Bruckner et al. | |
| 5,919,923 A | 7/1999 | Bruckner et al. | |
| 5,929,105 A | 7/1999 | Sternberg et al. | |
| 6,008,195 A * | 12/1999 | Selsted ........................ 514/2.7 |
| 6,274,614 B1 * | 8/2001 | Richter et al. ............... 514/410 |
| 6,620,929 B1 | 9/2003 | MacAlpine et al. | |
| 6,693,093 B2 * | 2/2004 | Chowdhary et al. .......... 514/185 |
| 7,022,843 B1 | 4/2006 | MacAlpine et al. | |
| 7,282,215 B2 * | 10/2007 | Chowdhary et al. .......... 424/450 |
| 2002/0061330 A1 | 5/2002 | Chowdhary et al. | |

FOREIGN PATENT DOCUMENTS

| | | | |
|---|---|---|---|
| WO | WO 98/346 | * | 8/1998 |
| WO | WO-98/34644 | | 8/1998 |
| WO | WO-99/18998 | | 4/1999 |
| WO | WO-99/51284 | | 10/1999 |
| WO | WO-01/85213 | | 11/2001 |
| WO | WO-01/97848 | | 12/2001 |

OTHER PUBLICATIONS

Alexandridis et al., Macromolecules (1994) 27:2414-2425.
Alison et al., Photochem. Photobiol. (1990) 52(3):501-507.
Bodmeier et al., (1995) 12(8):1211-1218.
Chow and Bernard, J. Pharm. Sci. (1980) 70(8):924-926.
Chowdhary, Photochemistry and Photobiology (1990) 5(4):395-399.
Collett et al., J. Pharm. Pharmacol. (1979) 31(Suppl.):P80.
Edsman et al., Eur. J. Pharm. Sci. (1998) 6:105-112.
Geran et al., Protocols for Screening Chemical Agents and Natural Products Against Animal Tumors and Other Biological Systems (Third Edition), Canc. Chemother. Reports, Part 3, 3:1-112.
Hunter et al., AIDS Research and Human Retroviruses (1994) 10(Supp. 2):S95-S98.
Kabanov et al., J. Contr. Rel. (1998) 22:141-158.
Kataoka et al., J. Controlled Release (1993) 24:119-132.
Krishna et al., Journal (1998) 52(6):331-336.
Melik-Nubarov et al., FEBS Lett. (1999) 446(1):194-198.
Mosmann, J. Immunol. Meth. (1983) 65:55-63.
Omelyanenko et al., Int. J. Cancer (1998) 75:600-608.
Peterson et al., Cancer Res. (1996) 56(17):3980-3985.
Redmond and Gamlin, Photochem. Photobiol. (1999) 70(4):391-475.

(Continued)

*Primary Examiner* — Blessing M Fubara
(74) *Attorney, Agent, or Firm* — Sterne, Kessler, Goldstein & Fox P.L.L.C.

(57) ABSTRACT

The invention is generally related to the field of photodynamic therapy by use of photosensitizers and stabilized formulations of the photosensitizers. These formulations may be used to deliver a photosensitizer as a pharmaceutical, agricultural, or industrial agent. The photosensitizer containing formulations and compositions of the invention comprise one or more block copolymers. Furthermore, the invention relates to processes for the production of, and application of, said formulations and compositions as photosensitizer drug delivery systems.

14 Claims, 2 Drawing Sheets

(56) References Cited

OTHER PUBLICATIONS

Richter et al., Proc. SPIE (1993) 2078:293-304.
Rudel, Biochem. J. (1974) 139:89-95.
Schmolka, in Polymers for Controlled Drug Delivery, Tarcha (Ed.), CRC Press, Boca Raton, FL (1991).
Siggel et al., J. Phys. Chem. (1996) 100(12):2070-2075.
Wurster, J. Amer. Pharm. Assoc. (1959) 48:451.

* cited by examiner

DRUG DELIVERY SYSTEMS FOR PHOTODYNAMIC THERAPY

CROSS-REFERENCE TO RELATED APPLICATIONS

This application is a continuation of U.S. Ser. No. 10/688,090 filed 17 Oct. 2003 which is a continuation of U.S. Ser. No. 09/851,641 filed 8 May 2001 which is a non-provisional utility patent application that claims priority from United States provisional patent application U.S. Ser. No. 60/202,641, filed 8 May 2000. The contents of the applications listed in this paragraph are fully incorporated by reference herein.

TECHNICAL FIELD

The invention is generally related to the field of photodynamic therapy by use of photosensitizers and stabilized formulations of the photosensitizers. These formulations may be used to deliver a photosensitizer as a pharmaceutical, agricultural, or industrial agent. The photosensitizer containing formulations and compositions of the invention comprise one or more block copolymers. Additionally the invention relates to the inclusion of one or more solid supports in such formulations and compositions and/or the deposition of such formulations and compositions on one or more solid supports. The inclusion of solid supports increases the ease of hydrating the formulation or composition, which improves the effectiveness of the formulations and compositions as delivery vehicles for photosensitizers. Furthermore, the invention relates to processes for the production of, and application of, said formulations and compositions as photosensitizer drug delivery systems.

BACKGROUND OF THE INVENTION

Conventional photodynamic therapy (PDT) generally involves the administration of a photosensitizer drug or compound to a recipient, either locally or systemically, followed by irradiation with light that is capable of being absorbed by the photosensitizer in the tissue or organ to be treated. The mode of photosensitizer drug delivery is of paramount importance. The drug not only has to be in a form suitable for administration, but also in a form that can readily undergo cellular internalization at the target site, preferably with some degree of selectivity over normal tissues.

There are multiple means of delivering pharmaceutical agents. These range from simple intravenous injection of solutions, emulsions, liposomes and microspheres to complex implantable time-release carriers. Photofrin® (QLT PhotoTherapeutics Inc., Vancouver, B.C., Canada, QLT) has been delivered successfully as part of a simple aqueous solution. Such aqueous solutions may not be suitable for hydrophobic photosensitizer drugs of interest that have a tetra- or poly-pyrrole-based structure. These drugs have an inherent tendency to aggregate by molecular stacking, which can severely curtail subsequent photosensitization processes (Siggel et al. *J. Phys. Chem.* 100(12):2070-2075, December 1996). One approach for maintaining lipid soluble (hydrophobic) drugs in non-aggregated form is to formulate them in a hydrophobic liposomal bilayer.

Liposomal formulations of some hydrophobic photosensitizing drugs, such as benzoporphyrin derivative monoacid-A (BPD-MA, Verteporfin®, QLT, Vancouver, Canada) and zinc phthalocyanine (CIBA-Geigy Ltd., Basel, Switzerland) are known. The liposome in the case of BPD-MA acts as a passive delivery agent, transferring the photosensitizer to plasma lipoproteins, such as low density lipoproteins (LDL), immediately upon injection into the blood stream. The higher surface expression of LDL receptors in rapidly proliferating tissues affords a level of selectivity to localization of hydrophobic LDL associated drugs at target sites for PDT. Though liposomal formulations have been successfully used for BPD-MA, they have been found unsatisfactory for other, newer photosensitizers developed for PDT in terms of drug loading, formulation stability and in vivo drug delivery. These photosensitizers are hydrophobic in nature and have properties that promote considerably greater molecular stacking interactions; thus, drug aggregation was found to take place even within the liposomal bilayer.

Biocompatible block copolymers are receiving increasingly wider usage in the pharmaceutical industry to enhance drug solubility and bioavailability (reviewed by Schmolka, Chapter 10, pp 189-214, in Tarcha (Ed.) *Polymers for Controlled Drug Delivery*, CRC Press, Boch Raton, Fla., 1991). This usage has included administration of a number of hydrophobic anti-cancer drugs. In the field of PDT, drug delivery using a two step conjugation of block copolymer N-(2-hydroxypropyl)methacrylamide (HPMA) to photosensitizer drug (Peterson et al. *Cancer Res*. 56(17):3980-3985, 1996) and, additionally, to antibodies (Omelyanenko et al. *Int, J. Cancer*. 75:600-608, 1998) have been conducted. HPMA conjugated to photosensitizer drugs, adriamycin or meso chlorin $e_6$ (Mce$_6$), and then to antibodies, for homing the drug to cancer cells, were found to be more effective than without the antibodies (Omelyanenko et al. Supra).

In the field of PDT, there is a continuing need for a drug delivery system that is simple, non-toxic, chemically inert, economical and can easily be used for formulating different types of photosensitizers. Requirements for a photosensitizer formulation include not only maintaining the drug in a relatively non-aggregated form, but also to achieve effective delivery to target site. The end-product should ideally have an extended shelf life (preferably as a solid state formulation) and be easy to reconstitute for administration. To prevent embolisms, particle size for a parenteral formulation must not exceed 1 μm. In the event that the formulation should prove to be unstable to autoclaving or gamma-radiation, particle size must be less than 0.2 μm in order to allow filter sterilization. Other requirements for a parenteral formulation include that they are sterile, isotonic, contain non-toxic components (biodegradable or readily excreted) and have physical and chemical stability. The end-product should ideally have an extended shelf life (preferably as a solid state formulation). All formulations, whether parenteral or otherwise, must be easily hydrated or reconstituted and be stable prior to administration and display effective delivery and performance at the target site, preferably with selective localization over normal tissues.

SUMMARY OF THE INVENTION

The present invention provides compositions and methods for drug formulations, storage and delivery methods useful for photodynamic therapy (PDT) utilizing photosensitizer drugs and one or more block copolymers as carriers. It has been discovered that these copolymers have wide ranging properties and have the potential to address many needs and formulation requirements of photosensitizer drug delivery systems. The copolymers are simple to use, non-toxic, chemically inert, economical, and can easily be used for formulating a wide range of photosensitizing drugs in a form that is readily taken up by the target cells. It has also been discovered that incorporation of hydrophobic photosensitizer drugs in block copolymers can be an effective technique for maintaining the drugs in a non-aggregated form by forming simple micelle, emulsion or gel complexes. Additionally, it has been discovered that incorporation of hydratable solid-supports in such formulations improves their hydration. In one embodiment, the invention is directed to a photosensitizer carrier composition comprising (a) one or more photosensitizer and (b) one or more block copolymer in liquid form capable of forming a complex with said photosensitizer and wherein said copolymer is i) not an amphiphilic polymer of polystyrene sodium sulphonate and vinyl naphthalene, and ii) not poloxamer 188.

The present invention also provides methods for photosensitizer drug release in a form suitable for administration to subjects undergoing photodynamic therapy. The invention further provides methods of preparing the aforementioned block copolymer comprising photosensitizer formulations. These methods comprise combining a photosensitizer and one or more block copolymers followed by conversion into a solid form. The solid form formulation containing the photosensitizer and block copolymer complex may remain as a solid or be optionally hydrated with an aqueous solution for storage or application. The formulation, either before or after hydration, may be further formulated with other pharmaceutically acceptable agents; alternatively, the formulation may be further processed before use for purposes such as size reduction. Preferably, the solid form or hydrated formulation will be separated into doses appropriate for administering an effective amount of the photosensitizer to a subject.

Furthermore, the invention provides compositions and methods for formulating a photosensitizer drug and block copolymer complex deposited on or encapsulated by a solid-support. Hydration of the complex results in a non-aggregated photosensitizer drug formulation.

DETAILED DESCRIPTION OF THE INVENTION

Definitions

Figure 1:
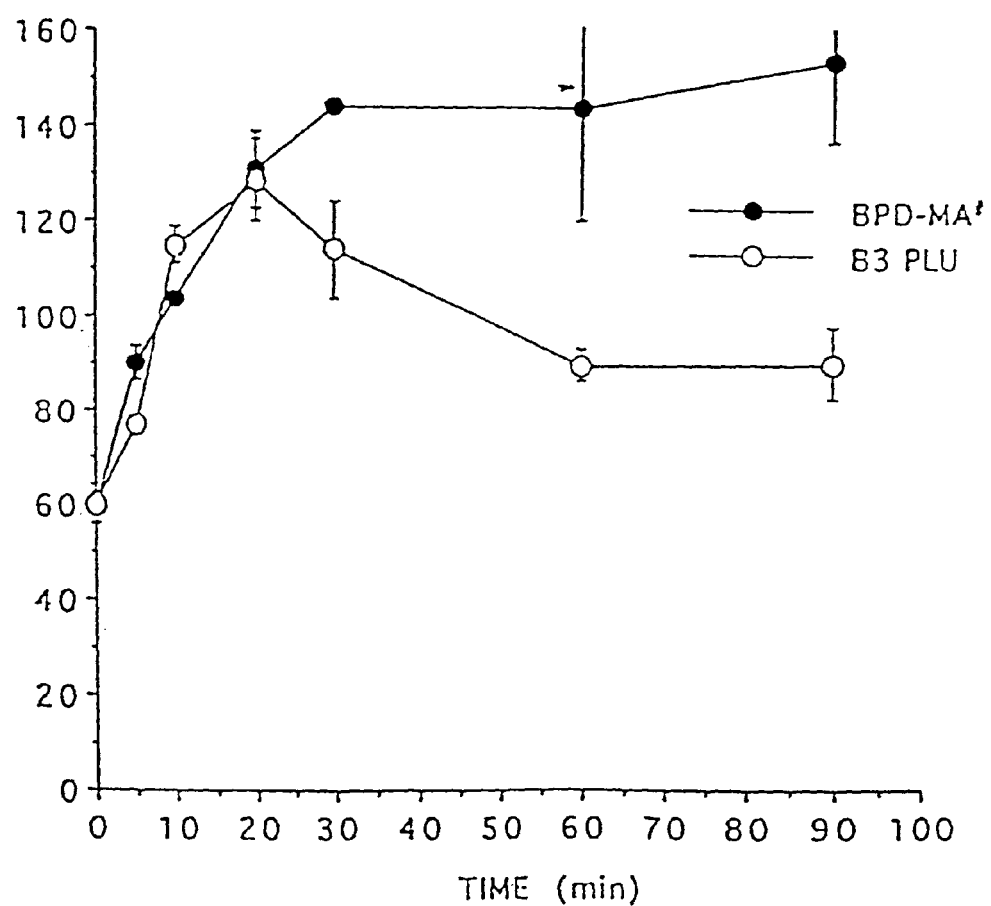
FIG. 1 is a graphical representation of in vitro cellular uptake of the photosensitizer B-B3 using block copolymer and liposomal formulations. Uptake of a copolymer Pluronic® P123 formulation was very rapid compared to the BPD-MA liposomal formulation. 50% uptake level was observed to be close to 'zero' incubation time, with uptake of B-B3 peaking in about 20 min. In comparison, BPD-MA achieved saturation level at 30 min, with 50% uptake in approximately 5 min.

Prior to setting forth the invention, it may be helpful to an understanding thereof to first set forth definitions of certain terms that will be used hereinafter.

"Block copolymer" and "copolymer" refer to carriers and carrier agents comprising any variation of two or more covalently linked blocks. The copolymers may be symmetric or asymmetric, amphiphilic (containing both hydrophilic and hydrophobic chemical groups), graft, or random. The blocks are linked by any appropriate linkage, including, but not limited to, —$CH_2$—, —O—, —NH—, carbonyl, ester, amide, and imide linkages. The carriers may or may not be charged, and preferably comprise two or three blocks. Preferably, the copolymers are symmetric or non-symmetric type triblock copolymers, which may be represented as A-B-A and A-B-A', respectively.

The carriers of the invention include poloxamers, or "PEO-PPO-PEO", which are symmetrical triblock copolymers of polyoxyethylene (PEO, EO) and polyoxypropylene (PPO, PO) denoted as PEO-PPO-PEO or $(EO)_{n1}(PO)_m(EO)_{n2}$ or $HO(C_2H_4O)_a(C_3H_6O)_b(C_2H_4O)_cH$. These copolymers are commercially available and have been well characterized in the art. Examples are the poloxamers sold under various trademarks, such as Pluronic® (BASF Corp.) or Synperonics® (ICI).

Also within the scope of the invention are amphiphilic copolymers as described in WO 99/18998 (or its corresponding U.S. Patent, if any), which is hereby incorporated by reference in its entirety as if fully set forth. Explicitly excluded from inclusion for use alone as a "block copolymer" or "copolymer" of the invention, however, is an amphiphilic polymer of polystyrene sodium sulphonate and vinyl naphthalene when the photosensitizer used in the invention is 5,10,15,20 tetrakis phenyl porphyrin. This specific amphiphilic polymer may also be excluded from inclusion for use alone when other photosensitizers are used in the invention. Thus 5,10,15,20 tetrakis phenyl porphyrin may be used in the invention if other copolymers or other photosensitizers or medicaments are used.

Another "block copolymer" that may be excluded from inclusion for use alone as a copolymer of the invention is Pluronic® F68 when hematoporphyrin derivatives are used as the medicament. Thus this poloxamer may be used as part of formulations containing additional agents, such as those for forming emulsions, but preferably not fluorocarbons such as FC43, PP11, and PP25.

In addition to copolymers, carriers and carrier agents of the invention include lipid compounds capable of forming or being associated with liposomes. In applications of the invention relating to liposome preparation, the associated or incorporated medicament is preferably limited either to photosensitizers or the use of exosupports. Carriers of the invention may be in a "liquid form", which includes any liquid or liquefied form of the carrier. Examples of the "liquid form" of carriers are the carriers dissolved in solution and the carrier in a liquefied form, such as in melted or molten forms. Preferred dissolved forms are prepared by solubilizing copolymers in appropriate solvents, preferably volatile solvents.

After formulation with a medicament of interest, the carrier may be converted to a "solid form" by removal of solvent or otherwise solidification of the carrier. Solvent removal may be by any means known in the art, including, but not limited to, spray drying, lyophilization, heating, and application of a vacuum. Solidification, especially of carriers in a liquefied form, may be by any means known in the art. These include, but are not limited to, cooling or hardening in the presence of a medicament or solid carrier.

"Complex" and "complexes" refer to stable micellar, emulsion, gel, matrix or transition phases between the defined states formed when a block copolymer and a medicament or photosensitizer associate to result in such forms. In some instances, formulation of such complexes requires the presence of additional agents that participate in the formation of micellar, emulsion, gel, matrix or transition phase structures in solution. Examples of such agents include oils or other lipids. The complexes of the invention may optionally include pharmaceutically acceptable excipients. They may also include adjuvants.

"Green porphyrins" refer to porphyrin derivatives obtained by reacting a porphyrin nucleus with an alkyne in a Diels-Alder type reaction to obtain a mono-hydrobenzoporphyrin.

"Solid support" or "support" refers to solid material with which a medicament (or photosensitizer) and carrier mixture may become associated. In cases of the mixture being in a solvent system, the association predominantly occurs upon solvent removal. The solid materials of the invention are normally not soluble in a solvent system solubilizing the medicament (or photosensitizer) and carrier mixture. Of course combinations of solid support materials may be used in association with any medicament/carrier mixture.

In another aspect of the invention, the carrier in a molten or other liquefied form acts as a "solvent" for hydrophobic medicaments such as some photosensitizers, thus obviating the need for solvent removal to prepare the medicament/carrier mixture. Such "solvent" carriers in their molten, melted, or other liquefied form may be readily combined with a medicament of interest. Examples of particularly excellent combinations using a "solvent" carrier as solvent include poloxamers or polyethylene glycols (PEGs) as the "solvent" carrier with photosensitizers. The ability to avoid extraneous solvent use is advantageous for ecological, health, safety, and disposal considerations. It is also beneficial in simplifying the processes involved (i.e. need for special precautions, handling and/or instrumentation) in preparing the compositions of the invention.

The compositions and methods of the invention may also serve to prepare a medicament in a "non-aggregated" form defined as that in which a medicament (i.e. photosensitizer) does not exhibit sufficient strong intermolecular interactions with other medicament molecules to result in significant aggregation.

The present invention provides compositions and methods for drug formulation as well as delivery methods useful for photodynamic therapy utilizing photosensitizers. Preferably, such compositions and methods comprise one or more of block copolymers as the carrier to address the needs described above. The photosensitizer and copolymer formulations of the invention include photosensitizer carrier compositions.

For example, one aspect of the present invention provides a composition for formulating photosensitizers. This composition comprises a photosensitizer drug and one or more block copolymers capable of forming complexes with the drug.

Another aspect of the present invention provides a method for formulating a photosensitizer comprising a) combining the photosensitizer with one or more desired block copolymers in liquid form, and b) solidifying, optionally by drying, the mixture to produce a complex of photosensitizer and block copolymer. The complex may then be subsequently hydrated with an aqueous solution to form photosensitizer-carrier complexes, which may be administered in an effective amount to a subject undergoing photodynamic therapy.

The compositions and methods of the present invention further include administration of simple formulations of photosensitizer compounds for recipients undergoing PDT treatment. The following describes the photosensitizers, methods of administration, compositions, formulations and storage and handling of the present invention. Experimental data are also presented and described.

A. Photosensitizers

The invention may be practiced with a variety of synthetic and naturally occurring pyrrole based photosensitizers, this includes pro-drugs such as 5-aminolevulinic acid, porphyrins and porphyrin derivatives e.g. chlorins, bacteriochlorins, isobacteriochlorins, phthalocyanine and naphthalocyanines and other tetra- and poly-macrocyclic compounds, and related compounds (e.g. pyropheophorbides, sapphyrins and texaphyrins) and metal complexes (such as, but not limited by, tin, aluminum, zinc, lutetium). Tetrahydrochlorins, purpurins, porphycenes, and phenothiaziniums are also within the scope of the invention.

Particularly preferred photosensitizers include green porphyrins such as BPD-MA, EA6 and B3. Generally, any polypyrrolic macrocyclic photosensitive compound that is hydrophobic can be used in the invention. Examples of these and other photosensitizers for use in the present invention include, but are not limited to, angelicins, some biological macromolecules such as lipofuscin; photosystem II reaction centers; and D1-D2-cyt b-559 photosystem II reaction centers, chalcogenapyrillium dyes, chlorins, chlorophylls, coumarins, cyanines, ceratin DNA and related compounds such as adenosine; cytosine; 2'-deoxyguanosine-5'-monophosphate; deoxyribonucleic acid; guanine; 4-thiouridine; 2'-thymidine 5'-monophosphate; thymidylyl(3'-5')-2'-deoxyadenosine; thymidylyl(3'-5')-2'-deoxyguanosine; thymine; and uracil, certain drugs such as adriamycin; afloqualone; amodiaquine dihydrochloride; chloroquine diphosphate; chlorpromazine hydrochloride; daunomycin; daunomycinone; 5-iminodaunomycin; doxycycline; furosemide; gilvocarcin M; gilvocarcin V; hydroxychloroquine sulfate; lumidoxycycline; mefloquine hydrochloride; mequitazine; merbromin (mercurochrome); primaquine diphosphate; quinacrine dihydrochloride; quinine sulfate; and tetracycline hydrochloride, certain flavins and related compounds such as alloxazine; flavin mononucleotide; 3-hydroxyflavone; limichrome; limiflavin; 6-methylalloxazine; 7-methylalloxazine; 8-methylalloxazine; 9-methylalloxazine; 1-methyl limichrome; methyl-2-methoxybenzoate; 5-nitrosalicyclic acid; proflavine; and riboflavin, fullerenes, metalloporphyrins, metallophthalocyanines, methylene blue derivatives, naphthalimides, naphthalocyanines, certain natural compounds such as bis(4-hydroxy-3-methoxyphenyl)-1,6-heptadiene-3,5-dione; 4-(4-hydroxy-3-methoxyphenyl)-3-buten-2-one; N-formylkynurenine; kynurenic acid; kynurenine; 3-hydroxykynurenine; DL-3-hydroxykynurenine; sanguinarine; berberine; carmane; and 5,7,9(11),22-ergostatetraene-3 β-ol, nile blue derivatives, NSAIDs (nonsteroidal anti-inflammatory drugs), perylenequinones, phenols, pheophorbides, pheophytins, photosensitizer dimers and conjugates, phthalocyanines, porphycenes, porphyrins, psoralens, purpurins, quinones, retinoids, rhodamines, thiophenes, verdins, vitamins and xanthene dyes (Redmond and Gamlin, *Photochem. Photobiol.*, 70(4):391-475 (1999)).

Exemplary angelicins include 3-aceto-angelicin; angelicin; 3,4'-dimethyl angelicin; 4,4'-dimethyl angelicin; 4,5'-dimethyl angelicin; 6,4'-dimethyl angelicin; 6,4-dimethyl angelicin; 4,4',5'-trimethyl angelicin; 4,4',5'-trimethyl-1'-thioangelicin; 4,6,4'-trimethyl-1'-thioangelicin; 4,6,4'-trimethyl angelicin; 4,6,5'-trimethyl-1'-thioangelicin; 6,4,4'-trimethyl angelicin; 6,4',5'-trimethyl angelicin; 4,6,4',5'-tetramethyl-1'-thioangelicin; and 4,6,4',5'-tetramethyl angelicin.

Exemplary chalcogenapyrillium dyes include pyrilium perchlorate, 4,4'-(1,3-propenyl)-bis[2,6-di(1,1-dimethyl-ethyl)]-; pyrilium perchlorate, 2,6-bis(1,1-dimethyl-ethyl)-4-[1-[2,6-bis(1,1-dimethyl-ethyl)selenopyran-4-ylidene]-3-propenyl-; pyrilium hexofluoro phosphate, 2,6-bis-(1,1-dimethyl-ethyl)-selenopyran-4-ylidene]-3-propenyl-; pyrilium hexofluoro phosphate, 2,6-bis(1,1-dimethyl-ethyl)-selenopyran-4-ylidene]-3-propenyl-; pyrilium perchlorate, 2,6-bis(1,1-dimethyl-ethyl)-4-[1-[2,6-bis(1,1-dimethyl-ethyl)telluropyran-4-ylidene]-3-propenyl-; pyrilium hexofluoro phosphate, 2,6-bis(1,1-dimethyl-ethyl)-4-[1-[2,6-bis(1,1-dimethyl-ethyl)telluropyran-4-ylidene]-3-propenyl-; pyrilium perchlorate, 2,6-bis(1,1-dimethyl-ethyl)-4-[1-[2,6-bis(1,1-dimethyl-ethyl)thiapyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; selenopyrilium, 2,6-bis(1,1-dimethylethyl)-4-[1-[2,6-bis(1,1-dimethylethyl)selenopyran-4-ylidene]-3-propenyl]-; selenopyrilium percheorate, 2,6-bis(1,1-dimethyl-ethyl)-4-[1-[2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-butenyl)]-; selenopyrilium hexofluoro phosphate, 2,6-bis(1,1-dimethyl-ethyl)-4-[2-[2,6-bis(1,1-dimethyl-ethyl)selenopyran-4-ylidene]-4-(2-pentenyl)]-; telluropyril tetrafluoroborate, 2,6-bis(1,1-dimethylethyl)-4-[1-[2,6-bis(1,1-dimethyl-ethyl)-telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]-3-propenyl]-; telluropyrilium hexofluoro phosphate, 2,6-bis(1,1-dimethyl-ethyl)-4-[1-[2,6-bis(1,1-dimethyl-ethyl)telluropyran-4-ylidene]ethyl-; telluropyrilium hexofluoro phosphate, 2,6-bis(1,1-dimethyl-ethyl)-4-[1-[2,6-bis(1,1-dimethyl-ethyl)-telluropyran-4-ylidene]methyl-; thiopyrilium hexofluoro phosphate, 2,6-bis(1,1-dimethyl-ethyl)-4-[1-[2,6-bis(1,1-dimethyl-ethyl)thiopyran-4-ylidene]-3-propenyl]-; thiopyrilium hexofluoro phosphate, 2,6-bis(1,1-dimethyl-ethyl)-4-[1-[2,6-bis(1,1-dimethyl-ethyl)selenopyran-4-ylidene]-3-propenyl]-; and thiopyrilium hexofluoro phosphate, 2,6-bis(1,1-dimethyl-ethyl)-4-[1-[2,6-bis(1,1-dimethyl-ethyl)telluropyran-4-ylidene]-3-propenyl]-.

Exemplary chlorins dyes include 5-azachlorin dimethyl ester derivative; 5,10,15,20-tetrakis-(m-hydroxyphenyl)bacteriochlorin; benzoporphyrin derivative monoacid ring A; benzoporphyrin derivative monoacid ring-A; porphine-2,18-dipropanoic acid, 7-[2-dimethyl-amino)-2-oxoethyl]-8-ethylidene-7,8-dihydro-3,7,12,17-tetramethyl, dimethylester; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z; porphine-2,18-dipropanoic acid, 7-[2-dimethyl-amino)-2-oxoethyl]-8-ethylidene-8-ethyl-7,8-dihydro-3,7,12,17-tetramethyl, dimethylester Z ECHL; porphine-2,18-dipropanoic acid, 7-[2-dimethyl-amino)-2-oxoethyl]-8-ethylidene-8-n-heptyl-7,8-dihydro-3,7,12,17-tetramethyl, dimethylester Z; tin (II) porphine-2,18-dipropanoic acid, 7-[2-(dimethylamino-2-oxoethyl]-8-ethylidene-8-n-heptyl-7,8-dihydro-3,7,12,17-tetramethyl, dimethylester Z; chlorin $e_6$; chlorin $e_6$ dimethyl ester; chlorin $e_6$ $k_3$; chlorin $e_6$ monomethyl ester; chlorin $e_6$ $Na_3$; chlorin $p_6$; chlorin $p_6$-trimethylester; chlorin derivative zinc (II) porphine-2,18-dipropanoic acid, 7-[2-(dimethylamino)-2-oxoethyl]-8-ethylidene-8-n-heptyl-7,8-dihydro-3,7,12,17-tetramethyl, dimethylester Z; $13^1$-deoxy-20-formyl-vic-dihydroxy-bacteriochlorin di-tert-butyl aspartate; $13^1$-deoxy-20-formyl-4-keto-bacteriochlorin di-tert-butyl aspartate; di-L-aspartyl chlorin $e_6$; mesochlorin; 5,10,15,20-tetrakis-(m-hydroxyphenyl)chlorin; meta-(tetrahydroxyphenyl)chlorin; methyl-$13^1$-deoxy-20-fornyl-4-keto-bacteriochlorin; mono-L-aspartyl chlorin $e_6$; photoprotoporphyrin IX dimethyl ester; phycocyanobilin dimethyl ester; protochlorophyllide a; tin (IV) chlorin $e_6$; tin chlorin $e_6$; tin L-aspartyl chlorin $e_6$; tin octaethyl-benzochlorin; tin (IV) chlorin; zinc chlorin $e_6$; and zinc L-aspartyl chlorin $e_6$.

Exemplary chlorophylls dyes include chlorophyll a; chlorophyll b; oil soluble chlorophyll; bacteriochlorophyll a; bacteriochlorophyll b; bacteriochlorophyll c; bacteriochlorophyll d; protochlorophyll; protochlorophyll a; amphiphilic chlorophyll derivative 1; and amphiphilic chlorophyll derivative 2.

Exemplary coumarins include 3-benzoyl-7-methoxycoumarin; 7-diethylamino-3-thenoylcoumarin; 5,7-dimethoxy-3-(1-naphthoyl)coumarin; 6-methylcoumarin; 2H-selenolo[3,2-g][1]benzopyran-2-one; 2H-selenolo[3,2-g][1]benzothiopyran-2-one; 7H-selenolo[3,2-g][1]benzoselenopyran-7-one; 7H-selenopyrano[3,2-f][1]benzofuran-7-one; 7H-selenopyrano[3,2-f][1]benzo-thiophene-7-one; 2H-thienol[3,2-g][1]benzopyran-2-one; 7H-thienol[3,2-g][1]benzothiopyran-7-one; 7H-thiopyrano[3,2-f][1]benzofuran-7-one; coal tar mixture; khellin; RG708; RG277; and visnagin.

Exemplary cyanines include benzoselenazole dye; benzoxazole dye; 1,1'-diethyloxacarbocyanine; 1,1'-diethyloxadicarbocyanine; 1,1'-diethylthiacarbocyanine; 3,3'-dialkylthiacarbocyanines (n=2-18); 3,3'-diethylthiacarbocyanine iodide; 3,3'-dihexylselenacarbocyanine; kryptocyanine; MC540 benzoxazole derivative; MC540 quinoline derivative; merocyanine 540; and meso-ethyl, 3,3'-dihexylselenacarbocyanine.

Exemplary fullerenes include $C_{60}$; $C_{70}$; $C_{76}$; dihydrofullerene; 1,9-(4-hydroxy-cyclohexano)-buckminster-fullerene; [1-methyl-succinate-4-methyl-cyclohexadiene-2, 3]-buckminster-fullerene; and tetrahydro fullerene.

Exemplary metalloporphyrins include cadmium (II) chlorotexaphyrin nitrate; cadmium (II) meso-diphenyl tetrabenzoporphyrin; cadmium meso-tetra-(4-N-methylpyridyl)-porphine; cadmium (II) texaphyrin; cadmium (II) texaphyrin nitrate; cobalt meso-tetra-(4-N-methylpyridyl)-porphine; cobalt (II) meso(4-sulfonatophenyl)-porphine; copper hematoporphyrin; copper meso-tetra-(4-N-methylpyridyl)-porphine; copper (II) meso(4-sulfonatophenyl)-porphine; Europium (III) dimethyltexaphyrin dihydroxide; gallium tetraphenylporphyrin; iron meso-tetra(4-N-methylpyridyl)-porphine; lutetium (III) tetra(N-methyl-3-pyridyl)-porphyrin chloride; magnesium (II) meso-diphenyl tetrabenzoporphyrin; magnesium tetrabenzoporphyrin; magnesium tetraphenylporphyrin; magnesium (II) meso(4-sulfonatophenyl)-porphine; magnesium (II) texaphyrin hydroxide metalloporphyrin; magnesium meso-tetra-(4-N-methylpyridyl)-porphine; manganese meso-tetra-(4-N-methylpyridyl)-porphine; nickel meso-tetra(4-N-methylpyridyl)-porphine; nickel (II) meso-tetra(4-sulfonatophenyl)-porphine; palladium (II) meso-tetra-(4-N-methylpyridyl)-porphine; palladium meso-tetra-(4-N-methylpyridyl)-porphine; palladium tetraphenylporphyrin; palladium (II) meso(4-sulfonatophenyl)-porphine; platinum (II) meso(4-sulfonatophenyl)-porphine; samarium (II) dimethyltexaphyrin dihydroxide; silver (II) meso(4-sulfonatophenyl)-porphine; tin (IV) protoporphyrin; tin meso-tetra-(4-N-methylpyridyl)-porphine; tin meso-tetra(4-sulfonatophenyl)-porphine; tin (IV) tetrakis(4-sulfonatophenyl) porphyrin dichloride; zinc (II) 15-aza-3,7,12,18-tetramethyl-porphyrinato-13,17-diyl-dipropionic acid-dimethylester; zinc (II) chlorotexaphyrin chloride; zinc coproporphyrin III; zinc (II) 2,11,20,30-tetra-(1,1-dimethyl-ethyl)tetranaphtho(2,3-b:2',3'-g:2"3"-1:2"'3"'-q)porphyrazine; zinc (II) 2-(3-pyridyloxy)benzo[b]-10,19,28-tri(1,1-dimethylethyl)trinaphtho[2',3'-g:2"3"1::2"',3"'-q] porphyrazine; zinc (II) 2,18-bis-(3-pyridyloxy)dibenzo[b,l]-10,26-di(1,1-dimethyl-ethyl)dinaphtho[2',3'-g:2"',3"'-q] porphyrazine; zinc (II) 2,9-bis-(3-pyridyloxy)dibenzo[b,g]-17,26-di(1,1-dimethyl-ethyl)dinaphtho[2",3'-1:2"',3"'-q] porphyrazine; zinc (II) 2,9,16-tris-(3-pyridyloxy)tribenzo[b,g,l]-24=(1,1-dimethyl-ethyl)naphtho[2"',3"'-q] porphyrazine; zinc (II) 2,3-bis-(3-pyridyloxy)benzo[b]-10,19,28-tri(1,1-dimethyl-ethyl)trinaphtho[2',3'-g:2"',3"'1:2"', 3"'-q]porphyrazine; zinc (II) 2,3,18,19-tetrakis-(3-pyridyloxy)dibenzo[b,l]-10,26-di(1,1-dimethyl-ethyl) trinaphtho[2',3'-g:2"',3"'-q]porphyrazine; zinc (II) 2,3,9,10-tetrakis-(3-pyridyloxy)dibenzo[b,g]-17,26-di(1,1-dimethyl-ethyl)dinaphtho[2",3"-1:2"',3"'-q]porphyrazine; zinc (II) 2,3,9,10,16,17-hexakis-(3-pyridyloxy)tribenzo[b,g,l]-24-(1,1-dimethyl-ethyl)naphtho[2"',3"'-q]porphyrazine; zinc (II) 2-(3-N-methyl)pyridyloxy)benzo[b]-10,19,28-tri(1,1-dimethyl-ethyl)trinaphtho[2',3'-g:2",3"1:2"',3"'-q]porphyrazine monoiodide; zinc (II) 2,18-bis-(3-(N-methyl)pyridyloxy) dibenzo[b,l]-10,26-di(1,1-dimethylethyl)dinaphtho[2',3'-g: 2"',3"'-q]porphyrazine diiodide; zinc (II) 2,9-bis-(3-(N-methyl)pyridyloxy)dibenzo[b,g]-17,26-di(1,1-dimethylethyl) dinaphtho[2",3"-1:2"',3"'-q]porphyrazine diiodide; zinc (II) 2,9,16-tris-(3-(N-methyl-pyridyloxy)tribenzo[b,g,l]-24-(1, 1-dimethylethyl)naphtho[2"',3"'-q]porphyrazine triiodide; zinc (II) 2,3-bis-(3-(N-methyl)pyridyloxy)benzo[b]-10,19, 28-tri(1,1-dimethylethyl)trinaphtho[2',3'-g:2",3"-1:2"',3"'-q] porphyrazine diiodide; zinc (II) 2,3,18,19-tetrakis-(3-(N-methyl)pyridyloxy)dibenzo[b,l]-10,26-di(1,1-dimethyl) dinaphtho[2',3'-g:2"',3"'-q]porphyrazine tetraiodide; zinc (II) 2,3,9,10-tetrakis-(3-(N-methyl)pyridyloxy)dibenzo[g,g]-17, 26-di(1,1-dimethylethyl)dinaphtho[2",3"-1:2"',3"'-q]porphyrazine tetraiodide; zinc (II) 2,3,9,10,16,17-hexakis-(3-(N-methyl)pyridyloxy)tribenzo[b,g,l]-24-(1,1-dimethylethyl)naphtho[2"',3"'-q]porphyrazine hexaiodide; zinc (II) meso-diphenyl tetrabenzoporphyrin; zinc (II) meso-triphenyl tetrabenzoporphyrin; zinc (II) meso-tetrakis(2,6-dichloro-3-sulfonatophenyl) porphyrin; zinc (II) meso-tetra-(4-N-methylpyridyl)-porphine; zinc (II) 5,10,15,20-meso-tetra(4-octyl-phenylpropynyl)-porphine; zinc porphyrin c; zinc protoporphyrin; zinc protoporphyrin IX; zinc (II) meso-triphenyl-tetrabenzoporphyrin; zinc tetrabenzoporphyrin; zinc (II) tetrabenzoporphyrin; zinc tetranaphthaloporphyrin; zinc tetraphenylporphyrin; zinc (II) 5,10,15,20-tetraphenylporphyrin; zinc (II) meso (4-sulfonatophenyl)-porphine; and zinc (II) texaphyrin chloride.

Exemplary metallophthalocyanines include aluminum mono-(6-carboxy-pentyl-amino-sulfonyl)-trisulfo-phthalocyanine; aluminum di-(6-carboxy-pentyl-amino-sulfonyl)-trisulfophthalocyanine; aluminum (III) octa-n-butoxy phthalocyanine; aluminum phthalocyanine; aluminum (III) phthalocyanine disulfonate; aluminum phthalocyanine disulfonate; aluminum phthalocyanine disulfonate (cis isomer); aluminum phthalocyanine disulfonate (clinical prep.); aluminum phthalocyanine phthalimido-methyl sulfonate; aluminum phthalocyanine sulfonate; aluminum phthalocyanine trisulfonate; aluminum (III) phthalocyanine trisulfonate; aluminum (III) phthalocyanine tetrasulfonate; aluminum phthalocyanine tetrasulfonate; chloroaluminum phthalocyanine; chloroaluminum phthalocyanine sulfonate; chloroaluminum phthalocyanine disulfonate; chloroaluminum phthalocyanine tetrasulfonate; chloroaluminum-t-butyl-phthalocyanine; cobalt phthalocyanine sulfonate; copper phthalocyanine sulfonate; copper (II) tetra-carboxy-phthalocyanine; copper (II)-phthalocyanine; copper t-butyl-phthalocyanine; copper phthalocyanine sulfonate; copper (II) tetrakis-[methylenethio[(dimethylamino)methylidyne]]phthalocyanine tetrachloride; dichlorosilicon phthalocyanine; gallium (III) octa-n-butoxy phthalocyanine; gallium (II) phthalocyanine disulfonate; gallium phthalocyanine disulfonate; gallium phthalocyanine tetrasulfonate-chloride; gallium (II) phthalocyanine tetrasulfonate; gallium phthalocyanine trisulfonate-chloride; gallium (II) phthalocyanine trisulfonate; $GaPcS_1tBu_3$; $GaPcS_2tBu_2$; $GaPcS_3tBu_1$; germanium (IV) octa-n-butoxy phthalocyanine; germanium phthalocyanine derivative; silicon phthalocyanine derivative; germanium (IV) phthalocyanine octakis-alkoxy-derivatives; iron phthalocyanine sulfonate; lead (II) 2,3,9,10,16,17,23,24-octakis(3, 6-dioxaheptyloxy)phthalocyanine; magnesium t-butyl-phthalocyanine; nickel (II) 2,3,9,10,16,17,23,24-octakis(3,6-dioxaheptyloxy)phthalocyanine; palladium (II) octa-n-butoxy phthalocyanine; palladium (II) tetra(t-butyl)-phthalocyanine; (diol) (t-butyl)$_3$-phthalocyanato palladium (II); ruthenium (II) dipotassium[bis(triphenyl-phosphine-monosulphonate) phthalocyanine; silicon phthalocyanine bis (tri-n-hexyl-siloxy)-; silicon phthalocyanine bis(tri-phenyl-siloxy)-; $HOSiPcOSi(CH_3)_2(CH_2)_3N(CH_3)_2$; $HOSiPcOSi(CH_3)_2(CH_2)_3N(CH_2CH_3)_2$; $SiPc[OSi(CH_3)_2(CH_2)_3N(CH_3)_2]_2$; $SiPc[OSi(CH_3)_2(CH_2)_3N(CH_2CH_3)(CH_2)_2(CH_3)_2]_2$; tin (IV) octa-n-butoxy phthalocyanine; vanadium phthalocyanine sulfonate; zinc (II) octa-n-butoxy phthalocyanine; zinc (II) 2,3,9,10,16,17,23,24-octakis(2-ethoxy-ethoxy)phthalocyanine; zinc (II) 2,3,9,10,16,17,23,24-octakis(3,6-dioxaheptyloxy)phthalocyanine; zinc (II) 1,4,8,11, 15,18,22,25-octa-n-butoxy-phthalocyanine; zn (II) phthalocyanine-octabutoxy; zn (II) phthalocyanine; zinc phthalocyanine; zinc (II) phthalocyanine; zinc phthalocyanine and perdeuterated zinc phthalocyanine; zinc (II) phthalocyanine disulfonate; zinc phthalocyanine disulfonate; zinc phthalocyanine sulfonate; zinc phthalocyanine tetrabromo-; zinc (II) phthalocyanine tetra-t-butyl-; zinc (II) phthalocyanine tetra-(t-butyl)-; zinc phthalocyanine tetracarboxy-; zinc phthalocyanine tetrachloro-; zinc phthalocyanine tetrahydroxyl; zinc phthalocyanine tetraiodo-; zinc ((I) tetrakis-(1, 1-dimethyl-2-phthalimido)ethyl phthalocyanine; zinc (II) tetrakis-(1,1,1-dimethyl-2-amino)-ethyl-phthalocyanine;

zinc (II) phthalocyanine tetrakis(1,1-dimethyl-2-trimethyl ammonium)ethyl tetraiodide; zinc phthalocyanine tetrasulphonate; zinc phthalocyanine tetrasulfonate; zinc (II) phthalocyanine tetrasulfonate; zinc (II) phthalocyanine trisulfonate; zinc phthalocyanine trisulfonate; zinc (II) (t-butyl)$_3$-phthalocyanine diol; zinc tetradibenzobarreleno-octabutoxy-phthalocyanine; zinc (II) 2,9,16,23,-tetrakis-(3-(N-methyl) pyridyloxy)phthalocyanine tetraiodide; and zinc (II) 2,3,9, 10,16,17,23,24-octakis-(3-(N-methyl)pyridyloxy) phthalocyanine complex octaiodide; and zinc (II) 2,3,9,10, 16,17,23,24-octakis-(3-pyridyloxy)phthalocyanine.

Exemplary methylene blue derivatives include 1-methyl methylene blue; 1,9-dimethyl methylene blue; methylene blue; methylene blue (16 μM); methylene blue (14 μM); methylene violet; bromomethylene violet; 4-iodomethylene violet; 1,9-dimethyl-3-dimethyl-amino-7-diethyl-amino-phenothiazine; and 1,9-dimethyl-3-diethylamino-7-dibutyl-amino-phenothiazine.

Exemplary naphthalimides blue derivatives include N,N'-bis-(hydroperoxy-2-methoxyethyl)-1,4,5,8-naphthaldiimide; N-(hydroperoxy-2-methoxyethyl)-1,8-naphthalimide;

1,8-naphthalimide; N,N'-bis(2,2-dimethoxyethyl)-1,4,5,8-naphthaldiimide; and N,N'-bis(2,2-dimethylpropyl)-1,4,5,8-naphthaldiimide.

Exemplary naphthalocyanines include aluminum 1-butyl-chloronaphthalocyanine; silicon bis(dimethyloctadecylsiloxy) 2,3-naphthalocyanine; silicon bis(dimethyloctadecylsiloxy)naphthalocyanine; silicon bis(dimethylthexylsiloxy) 2,3-naphthalocyanine; silicon bis(dimethylthexylsiloxy) naphthalocyanine; silicon bis(t-butyldimethylsiloxy) 2,3-naphthalocyanine; silicon bis(tert-butyldimethylsiloxy) naphthalocyanine; silicon bis(tri-n-hexylsiloxy) 2,3-naphthalocyanine; silicon bis(tri-n-hexylsiloxy) naphthalocyanine; silicon naphthalocyanine; t-butylnaphthalocyanine; zinc (II) naphthalocyanine; zinc (II) tetraacetyl-amidonaphthalocyanine; zinc (II) tetraaminonaphthalocyanine; zinc (II) tetrabenzamidonaphthalocyanine; zinc (II) tetrahexylamidonaphthalocyanine; zinc (II) tetramethoxy-benzamidonaphthalocyanine; zinc (II) tetramethoxynaphthalocyanine; zinc naphthalocyanine tetrasulfonate; and zinc (II) tetradodecylamidonaphthalocyanine.

Exemplary nile blue derivatives include benzo[a]phenothiazinium, 5-amino-9-diethylamino-; benzo[a]phenothiazinium, 5-amino-9-diethylamino-6-iodo-; benzo[a]phenothiazinium, 5-benzylamino-9-diethylamino-; benzo[a]phenoxazinium, 5-amino-6,8-dibromo-9-ethylamino-; benzo[a]phenoxazinium, 5-amino-6,8-diiodo-9-ethylamino-; benzo[a]phenoxazinium, 5-amino-6-bromo-9-diethylamino-; benzo[a]phenoxazinium, 5-amino-9-diethylamino-(nile blue A); benzo[a]phenoxazinium, 5-amino-9-diethylamino-2,6-diiodo-; benzo[a]phenoxazinium, 5-amino-9-diethylamino-2,-iodo; benzo[a]phenoxazinium, 5-amino-9-diethylamino-6-iodo-; benzo[a]phenoxazinium, 5-benzylamino-9-diethylamino-(nile blue 2B); 5-ethylamino-9-diethylamino-benzo[a]phenoselenazinium chloride; 5-ethylamino-9-diethyl-aminobenzo[a]phenothiazinium chloride; and 5-ethylamino-9-diethyl-aminobenzo[a]phenoxazinium chloride.

Exemplary NSAIDs (nonsteroidal anti-inflammatory drugs) include benoxaprofen; carprofen; carprofen dechlorinated (2-(2-carbazolyl)propionic acid); carprofen (3-chloro-carbazole); chlorobenoxaprofen; 2,4-dichlorobenoxaprofen; cinoxacin; ciprofloxacin; decarboxy-ketoprofen; decarboxy-suprofen; decarboxy-benoxaprofen; decarboxy-tiaprofenic acid; enoxacin; fleroxacin; fleroxacin-N-oxide; flumequine; indoprofen; ketoprofen; lomefloxacin; 2-methyl-4-oxo-2H-1,2-benzothiazine-1,1-dioxide; N-demethyl fleroxacin; nabumetone; nalidixic acid; naproxen; norfloxacin; ofloxacin; pefloxacin; pipemidic acid; piroxicam; suprofen; and tiaprofenic acid.

Exemplary perylenequinones include hypericins such as hypericin; hypericin monobasic sodium salt; di-aluminum hypericin; di-copper hypericin; gadolinium hypericin; terbium hypericin, hypocrellins such as acetoxy hypocrellin A; acetoxy hypocrellin B; acetoxy iso-hypocrellin A; acetoxy iso-hypocrellin B; 3,10-bis[2-(2-aminoethylamino)ethanol] hypocrellin B; 3,10-bis[2-(2-aminoethoxy)ethanol]hypocrellin B; 3,10-bis[4-(2-aminoethyl)morpholine]hypocrellin B; n-butylaminated hypocrellin B; 3,10-bis(butylamine)hypocrellin B; 4,9-bis(butylamine)hypocrellin B; carboxylic acid hypocrellin B; cystamine-hypocrellin B; 5-chloro hypocrellin A or 8-chloro hypocrellin A; 5-chloro hypocrellin B or 8-chloro hypocrellin B; 8-chloro hypocrellin B; 8-chloro hypocrellin A or 5-chloro hypocrellin A; 8-chloro hypocrellin B or 5-chloro hypocrellin B; deacetylated aldehyde hypocrellin B; deacetylated hypocrellin B; deacetylated hypocrellin A; deacylated, aldehyde hypocrellin B; demethylated hypocrellin B; 5,8-dibromo hypocrellin A; 5,8-dibromo hypocrellin B; 5,8-dibromo iso-hypocrellin B; 5,8-dibromo[1,12-CBr=CMeCBr(COMe)]hypocrellin B; 5,8-dibromo[1,12-CHBrC(=CH$_2$)CBr(COMe)]hypocrellin B; 5,8-dibromo[1-CH$_2$COMe, 12-COCOCH$_2$Br-]hypocrellin B; 5,8-dichloro hypocrellin A; 5,8-dichloro hypocrellin B; 5,8-dichlorodeacytylated hypocrellin B; 5,8-diiodo hypocrellin A; 5,8-diiodo hypocrellin B; 5,8-diiodo[1,12-CH=CMeCH (COCH$_2$I$_2$)-]hypocrellin B; 5,8-diiodo[1,12-CH$_2$C(CH$_2$I)=C(COMe)-]hypocrellin B; 2-(N,N-diethylamino)ethylaminated hypocrellin B; 3,10-bis[2-(N,N-diethylamino)-ethylamine]hypocrellin B; 4,9-bis[2-(N,N-diethyl-amino)-ethylamine]iso-hypocrellin B; dihydro-1,4-thiazine carboxylic acid hypocrellin B; dihydro-1,4-thiazine hypocrellin B; 2-(N,N-dimethylamino)propylamine hypocrellin B; dimethyl-1,3,5,8,10,12-hexamethoxy-4,9-perylenequinone-6,7-diacetate; dimethyl-5,8-dihydroxy-1,3,10,13-tetramethoxy-4,9-perylenequinone-6,7-diacetate; 2,11-dione hypocrellin A; ethanolamine hypocrellin B; ethanolamine iso-hypocrellin B; ethylenediamine hypocrellin B; 11-hydroxy hypocrellin B or 2-hydroxy hypocrellin B; hypocrellin A; hypocrellin B; 5-iodo[1,12-CH$_2$C(CH$_2$I)=C(COMe)-]hypocrellin B; 8-iodo[1,12-CH$_2$C(CH$_2$I)=C(COMe)-]hypocrellin B; 9-methylamino iso-hypocrellin B; 3,10-bis[2-(N,N-methylamino) propylamine]hypocrellin B; 4,9-bis(methylamine iso-hypocrellin B; 14-methylamine iso-hypocrellin B; 4-methylamine iso-hypocrellin B; methoxy hypocrellin A; methoxy hypocrellin B; methoxy iso-hypocrellin A; methoxy iso-hypocrellin B; methylamine hypocrellin B; 2-morpholino ethylaminated hypocrellin B; pentaacetoxy hypocrellin A; PQP derivative; tetraacetoxy hypocrellin B; 5,8,15-tribromo hypocrellin B; calphostin C, Cercosporins such as acetoxy cercosporin; acetoxy iso-cercosporin; aminocercosporin; cercosporin; cercosporin+iso-cercosporin (1/1 molar); diaminocercosporin; dimethylcercosporin; 5,8-dithiophenol cercosporin; iso-cercosporin; methoxycercosporin; methoxy iso-cercosporin; methylcercosporin; noranhydrocercosporin; elsinochrome A; elsinochrome B; phleichrome; and rubellin A.

Exemplary phenols include 2-benzylphenol; 2,2'-dihydroxybiphenyl; 2,5-dihydroxybiphenyl; 2-hydroxybiphenyl; 2-methoxybiphenyl; and 4-hydroxybiphenyl.

Exemplary pheophorbides include pheophorbide a; methyl 13[1]-deoxy-20-formyl-7,8-vic-dihydro-bacterio-meso-pheophorbide a; methyl-2-(1-dodecyloxyethyl)-2-devinyl-pyropheophorbide a; methyl-2-(1-heptyl-oxyethyl)-2-devinyl-pyropheophorbide a; methyl-2-(1-hexyl-oxyethyl)-2-devinyl-pyropheophorbide a; methyl-2-(1-methoxy-ethyl)-2-devinyl-pyropheophorbide a; methyl-2-(1-pentyl-oxyethyl)-2-devinyl-pyropheophorbide a; magnesium methyl bacteriopheophorbide d; methyl-bacteriopheophorbide d; and pheophorbide.

Exemplary pheophytins include bacteriopheophytin a; bacteriopheophytin b; bacteriopheophytin c; bacteriopheophytin d; 10-hydroxy pheophytin a; pheophytin; pheophytin a; and protopheophytin.

Exemplary photosensitizer dimers and conjugates include aluminum mono-(6-carboxy-pentyl-amino-sulfonyl)-trisulfophthalocyanine bovine serum albumin conjugate; dihematoporphyrin ether (ester); dihematoporphyrin ether; dihematoporphyrin ether (ester)-chlorin; hematoporphyrin-chlorin ester; hematoporphyrin-low density lipoprotein conjugate; hematoporphyrin-high density lipoprotein conjugate; porphine-2,7,18-tripropanoic acid, 13,13'-(1,3-propanediyl)bis[3,8,12,17-tetramethyl]-; porphine-2,7,18-tripropanoic acid, 13,13'-(1,11-undecanediyl)bis[3,8,12,17-tetramethyl]-; porphine-2,7,18-tripropanoic acid, 13,13'-(1,6-hexanediyl)bis[3,8,12,17-tetramethyl]-; SnCe6-MAb conjugate 1.7:1; SnCe6-MAb conjugate 1.7:1; SnCe6-MAb conjugate 6.8:1; SnCe6-MAb conjugate 11.2:1; SnCe6-MAb conjugate 18.9:1; SnCe6-dextran conjugate 0.9:1; SnCe6-dextran conjugate 3.5:1; SnCe6-dextran conjugate 5.5:1; SnCe6-dextran conjugate 9.9:1; α-terthienyl-bovine serum albumin conjugate (12:1); α-terthienyl-bovine serum albumin conjugate (4:1); and tetraphenylporphine linked to 7-chloroquinoline.

Exemplary phthalocyanines include (diol) (t-butyl)$_3$-phthalocyanine; (t-butyl)$_4$-phthalocyanine; cis-octabutoxy-dibenzo-dinaphtho-porphyrazine; trans-octabutoxy-dibenzo-dinaphtho-porphyrazine; 2,3,9,10,16,17,23,24-octakis2-ethoxyethoxy)phthalocyanine; 2,3,9,10,16,17,23,24-octakis(3,6-dioxaheptyloxy)phthalocyanine; octa-n-butoxy phthalocyanine; phthalocyanine; phthalocyanine sulfonate; phthalocyanine tetrasulphonate; phthalocyanine tetrasulfonate; t-butyl-phthalocyanine; tetra-t-butyl phthalocyanine; and tetradibenzobarreleno-octabutoxy-phthalocyanine.

Exemplary porphycenes include 2,3-($2^3$-carboxy-$2^4$-methoxycarbonyl benzo)-7,12,17-tris(2-methoxyethyl)porphycene; 2-(2-hydroxyethyl)-7,12,17-tri(2-methoxyethyl)porphycene; 2-(2-hydroxyethyl)-7,12,17-tri-n-propyl-porphycene; 2-(2-methoxyethyl)-7,12,17-tri-n-propyl-porphycene; 2,7,12,17-tetrakis(2-methoxyethyl) porphycene; 2,7,12,17-tetrakis(2-methoxyethyl)-9-hydroxy-porphycene; 2,7,12,17-tetrakis(2-methoxyethyl)-9-methoxy-porphycene; 2,7,12,17-tetrakis(2-methoxyethyl)-9-n-hexyloxy-porphycene; 2,7,12,17-tetrakis(2-methoxyethyl)-9-acetoxy-porphycene; 2,7,12,17-tetrakis(2-methoxyethyl)-9-caproyloxy-porphycene; 2,7,12,17-tetrakis(2-methoxyethyl)-9-pelargonyloxy-porphycene; 2,7,12,17-tetrakis(2-methoxyethyl)-9-stearoyloxy-porphycene; 2,7,12,17-tetrakis(2-methoxyethyl)-9-(N-t-butoxycarbonylglycinoxy)porphycene; 2,7,12,17-tetrakis(2-methoxyethyl)-9-[4-((β-apo-7-carotenyl)benzoyloxyl-porphycene; 2,7,12,17-tetrakis(2-methoxyethyl)-9-amino-porphycene; 2,7,12,17-tetrakis(2-methoxyethyl)-9-acetamido-porphycene; 2,7,12,17-tetrakis(2-methoxyethyl)-9-glutaramido-porphycene; 2,7,12,17-tetrakis(2-methoxyethyl)-9-(methyl-glutaramido)-porphycene; 2,7,12,17-tetrakis(2-methoxyethyl)-9-(glutarimido)-porphycene; 2,7,12,17-tetrakis(2-methoxyethyl)-3-(N,N-dimethylaminomethyl)-porphycene; 2,7,12,17-tetrakis(2-methoxyethyl)-3-(N,N-dimethylaminomethyl)-porphycene hydrochloride; 2,7,12,17-tetrakis(2-ethoxyethyl)-porphycene; 2,7,12,17-tetra-n-propyl-porphycene; 2,7,12,17-tetra-n-propyl-9-hydroxy-porphycene; 2,7,12,17-tetra-n-propyl-9-methoxy-porphycene; 2,7,12,17-tetra-n-propyl-9-acetoxy porphycene; 2,7,12,17-tetra-n-propyl-9-(t-butyl glutaroxy)-porphycene; 2,7,12,17-tetra-n-propyl-9-(N-t-butoxycarbonylglycinoxy)-porphycene; 2,7,12,17-tetra-n-propyl-9-(4-N-t-butoxy-carbonyl-butyroxy)-porphycene; 2,7,12,17-tetra-n-propyl-9-amino-porphycene; 2,7,12,17-tetra-n-propyl-9-acetamido-porphycene; 2,7,12,17-tetra-n-propyl-9-glutaramido-porphycene; 2,7,12,17-tetra-n-propyl-9-(methyl glutaramido)-porphycene; 2,7,12,17-tetra-n-propyl-3-(N,N-dimethylaminomethyl)porphycene; 2,7,12,17-tetra-n-propyl-9,10-benzo porphycene; 2,7,12,17-tetra-n-propyl-9-p-benzoyl carboxy-porphycene; 2,7,12,17-tetra-n-propyl-porphycene; 2,7,12,17-tetra-t-butyl-3,6;13,16-dibenzo-porphycene; 2,7-bis(2-hydroxyethyl)-12,17-di-n-propyl-porphycene; 2,7-bis(2-methoxyethyl)-12,17-di-n-propyl-porphycene; and porphycene.

Exemplary porphyrins include 5-azaprotoporphyrin dimethylester; bis-porphyrin; coproporphyrin III; coproporphyrin III tetramethylester; deuteroporphyrin; deuteroporphyrin IX dimethylester; diformyldeuteroporphyrin IX dimethylester; dodecaphenylporphyrin; hematoporphyrin; hematoporphyrin (8 μM); hematoporphyrin (400 μM); hematoporphyrin (3 μM); hematoporphyrin (18 μM); hematoporphyrin (30 μM); hematoporphyrin (67 μM); hematoporphyrin (150 μM); hematoporphyrin IX; hematoporphyrin monomer; hematoporphyrin dimer; hematoporphyrin derivative; hematoporphyrin derivative (6 μM); hematoporphyrin derivative (200 μM); hematoporphyrin derivative A (20 μM); hematoporphyrin IX dihydrochloride; hematoporphyrin dihydrochloride; hematoporphyrin IX dimethylester; haematoporphyrin IX dimethylester; mesoporphyrin dimethylester; mesoporphyrin IX dimethylester; monoformyl-monovinyl-deuteroporphyrin IX dimethylester; monohydroxyethylvinyl deuteroporphyrin; 5,10,15,20-tetra(o-hydroxyphenyl)porphyrin; 5,10,15,20-tetra(m-hydroxyphenyl)porphyrin; 5,10,15,20-tetrakis-(m-hydroxyphenyl) porphyrin; 5,10,15,20-tetra(p-hydroxyphenyl)porphyrin; 5,10,15,20-tetrakis(3-methoxyphenyl)porphyrin; 5,10,15,20-tetrakis(3,4-dimethoxyphenyl)porphyrin; 5,10,15,20-tetrakis(3,5-dimethoxyphenyl)porphyrin; 5,10,15,20-tetrakis(3,4,5-trimethoxyphenyl)porphyrin; 2,3,7,8,12,13,17,18-octaethyl-5,10,15,20-tetraphenylporphyrin; Photofrin®; Photofrin® II; porphyrin c; protoporphyrin; protoporphyrin IX; protoporphyrin dimethylester; protoporphyrin IX dimethylester; protoporphyrin propylaminoethylformamide iodide; protoporphyrin N,N-dimethylaminopropylformamide; protoporphyrin propylaminopropylformamide iodide; protoporphyrin butylformamide; protoporphyrin N,N-dimethylamino-formamide; protoporphyrin formamide; sapphyrin 13,12,13,22-tetraethyl-2,7,18,23 tetramethyl sapphyrin-8,17-dipropanol; sapphyrin 23,12,13,22-tetraethyl-2,7,18,23 tetramethyl sapphyrin-8-monoglycoside; sapphyrin 3; meso-tetra-(4-N-carboxyphenyl)-porphine; tetra-(3-methoxyphenyl)-porphine; tetra-(3-methoxy-2,4-difluorophenyl)-porphine; 5,10,15,20-tetrakis(4-N-methylpyridyl)porphine; meso-tetra-(4-N-methylpyridyl)-porphine tetrachloride; meso-tetra(4-N-methylpyridyl)-porphine; meso-tetra-(3-N-methylpyridyl)-porphine; meso-tetra-(2-N-methylpyridyl)-porphine; tetra(4-N,N,N-trimethylanilinium)porphine; meso-tetra-(4-N,N,N"-trimethylamino-phenyl)porphine tetrachloride; tetranaphthaloporphyrin; 5,10,15,20-tetraphenylporphyrin; tetraphenylporphyrin; meso-tetra-(4-N-sulfonatophenyl)-porphine; tetraphenylporphine tetrasulfonate; meso-tetra(4-sulfonatophenyl)porphine; tetra(4-sulfonatophenyl)porphine; tetraphenylporphyrin sulfonate; meso-tetra(4-sulfonatophenyl)porphine; tetrakis(4-sulfonatophenyl)porphyrin; meso-tetra(4-sulfonatophenyl)porphine; meso(4-sulfonatophenyl)porphine; meso-tetra(4-sulfonatophenyl)porphine; tetrakis(4-sulfonatophenyl) porphyrin; meso-tetra(4-N-trimethylanilinium)-porphine; uroporphyrin; uroporphyrin I (17 μM); uroporphyrin IX; and uroporphyrin I (18 μM).

Exemplary psoralens include psoralen; 5-methoxypsoralen; 8-methoxypsoralen; 5,8-dimethoxypsoralen; 3-carbethoxypsoralen; 3-carbethoxy-pseudopsoralen; 8-hydroxypsoralen; pseudopsoralen; 4,5',8-trimethylpsoralen; allopsoralen; 3-aceto-allopsoralen; 4,7-dimethyl-allopsoralen; 4,7,4'-trimethyl-allopsoralen; 4,7,5'-trimethyl-allopsoralen; isopseudopsoralen; 3-acetoisopseudopsoralen; 4,5'-dimethyl-isopseudopsoralen; 5',7-dimethyl-isopseudopsoralen; pseudoisopsoralen; 3-acetopseudoisopsoralen; 3/4',5'-trimethyl-aza-psoralen; 4,4',8-trimethyl-5'-amino-methylpsoralen; 4,4',8-trimethyl-phthalamyl-psoralen; 4,5',8-trimethyl-4'-aminomethyl psoralen; 4,5',8-trimethyl-bromopsoralen; 5-nitro-8-methoxypsoralen; 5'-acetyl-4,8-dimethyl-psoralen; 5'-aceto-8-methyl-psoralen; and 5'-aceto-4,8-dimethyl-psoralen.

Exemplary purpurins include octaethylpurpurin; octaethylpurpurin zinc; oxidized octaethylpurpurin; reduced octaethylpurpurin; reduced octaethylpurpurin tin; purpurin 18; purpurin-18; purpurin-18-methyl ester; purpurin; tin ethyl etiopurpurin I; Zn(II) aetio-purpurin ethyl ester; and zinc etiopurpurin.

Exemplary quinones include 1-amino-4,5-dimethoxy anthraquinone; 1,5-diamino-4,8-dimethoxy anthraquinone; 1,8-diamino-4,5-dimethoxy anthraquinone; 2,5-diamino-1,8-dihydroxy anthraquinone; 2,7-diamino-1,8-dihydroxy anthraquinone; 4,5-diamino-1,8-dihydroxy anthraquinone; mono-methylated 4,5- or 2,7-diamino-1,8-dihydroxy anthraquinone; anthralin (keto form); anthralin; anthralin anion; 1,8-dihydroxy anthraquinone; 1,8-dihydroxy anthraquinone (Chrysazin); 1,2-dihydroxy anthraquinone; 1,2-dihydroxy anthraquinone (Alizarin); 1,4-dihydroxy anthraquinone (Quinizarin); 2,6-dihydroxy anthraquinone; 2,6-dihydroxy anthraquinone (Anthraflavin); 1-hydroxy anthraquinone (Erythroxy-anthraquinone); 2-hydroxy-anthraquinone; 1,2,5,8-tetra-hydroxy anthraquinone (Quinalizarin); 3-methyl-1,6,8-trihydroxy anthraquinone (Emodin); anthraquinone; anthraquinone-2-sulfonic acid; benzoquinone; tetramethyl benzoquinone; hydroquinone; chloro-hydroquinone; resorcinol; and 4-chlororesorcinol.

Exemplary retinoids include all-trans retinal; $C_{17}$ aldehyde; $C_{22}$ aldehyde; 11-cis retinal; 13-cis retinal; retinal; and retinal palmitate.

Exemplary rhodamines include 4,5-dibromo-rhodamine methyl ester; 4,5-dibromo-rhodamine n-butyl ester; rhodamine 101 methyl ester; rhodamine 123; rhodamine 6G; rhodamine 6G hexyl ester; tetrabromo-rhodamine 123; and tetramethyl-rhodamine ethyl ester.

Exemplary thiophenes include terthiophenes such as 2,2':5',2"-terthiophene; 2,2':5',2"-terthiophene-5-carboxamide; 2,2':5',2"-terthiophene-5-carboxylic acid; 2,2':5',2"-terthiophene-5-L-serine ethyl ester; 2,2':5',2"-terthiophene-5-N-isopropynyl-formamide; 5-acetoxymethyl-2,2':5',2"-terthiophene; 5-benzyl-2,2':5',2"-terthiophene-sulphide; 5-benzyl-2,2':5',2"-terthiophene-sulfoxide; 5-benzyl-2,2':5',2"-terthiophene-sulphone; 5-bromo-2,2':5',2"-terthiophene; 5-(butynyl-3'"-hydroxy)-2,2':5',2"-terthiophene; 5-carboxyl-5"-trimethylsilyl-2,2':5',2"-terthiophene; 5-cyano-2,2':5',2"-terthiophene; 5,5"-dibromo-2,2':5',2"-terthiophene; 5-(1'",1'"-dibromoethenyl)-2,2':5',2"-terthiophene; 5,5"-dibromo-2,2':5',2"-terthiophene; 5,5"-diformyl-2,2':5',2"-terthiophene; 5-difluoromethyl-2,2':5',2"-terthiophene; 5,5"-diiodo-2,2':5',2"-terthiophene; 3,3"-dimethyl-2,2':5',2"-terthiophene; 5,5"-dimethyl-2,2':5',2"-terthiophene; 5-(3'",3'"-dimethylacryloyloxymethyl)-2,2':5',2"-terthiophene; 5,5"-di-(t-butyl)-2,2':5',2"-terthiophene; 5,5"-dithiomethyl-2,2':5',2"-terthiophene; 3'-ethoxy-2,2':5',2"-terthiophene; ethyl 2,2':5',2"-terthiophene-5-carboxylic acid; 5-formyl-2,2':5',2"-terthiophene; 5-hydroxyethyl-2,2':5',2"-terthiophene; 5-hydroxymethyl-2,2':5',2"-terthiophene; 5-iodo-2,2':5',2"-terthiophene; 5-methoxy-2,2':5',2"-terthiophene; 3'-methoxy-2,2':5',2"-terthiophene; 5-methyl-2,2':5',2"-terthiophene; 5-(3'"-methyl-2'"-butenyl)-2,2':5',2"-terthiophene; methyl 2,2':5',2"-terthiophene-5-[3'"-acrylate]; methyl 2,2':5',2"-terthiophene-5-(3'"-propionate); N-allyl-2,2':5',2"-terthiophene-5-sulphonamide; N-benzyl-2,2':5',2"-terthiophene-5-sulphonamide; N-butyl-2,2':5',2"-terthiophene-5-sulphonamide; N,N-diethyl-2,2':5',2"-terthiophene-5-sulphonamide; 3,3',4',3"-tetramethyl-2,2':5',2"-terthiophene; 5-t-butyl-5"-trimethylsilyl-2,2':5',2"-terthiophene; 3-thiomethyl-2,2':5',2"-terthiophene; 5-thiomethyl-2,2':5',2"-terthiophene; 5-trimethylsilyl-2,2':5',2"-terthiophene, bithiophenes such as 2,2'-bithiophene; 5-cyano-2,2'-bithiophene; 5-formyl-2,2'-bithiophene; 5-phenyl-2,2'-bithiophene; 5-(propynyl)-2,2'-bithiophene; 5-(hexynyl)-2,2'-bithiophene; 5-(octynyl)-2,2'-bithiophene; 5-(butynyl-4"-hydroxy)-2,2'-bithiophene; 5-(pentynyl-5"-hydroxy)-2,2'-bithiophene; 5-(3",4"-dihydroxybutynyl)-2,2'-bithiophene derivative; 5-(ethoxybutynyl)-2,2'-bithiophene derivative, and misclaneous thiophenes such as 2,5-diphenylthiophene; 2,5-di(2-thienyl)furan; pyridine,2,6-bis(2-thienyl)-; pyridine, 2,6-bis(thienyl)-; thiophene, 2-(1-naphthalenyl)-; thiophene, 2-(2-naphthalenyl)-; thiophene, 2,2'-(1,2-phenylene)bis-; thiophene, 2,2'-(1,3-phenylene)bis-; thiophene, 2,2'-(1,4-phenylene)bis-; 2,2':5',2":5'",2'"-quaterthiophene; α-quaterthienyl; α-tetrathiophene; α-pentathiophene; α-hexathiophene; and α-heptathiophene.

Exemplary verdins include copro (II) verdin trimethyl ester; deuteroverdin methyl ester; mesoverdin methyl ester; and zinc methyl pyroverdin.

Exemplary vitamins include ergosterol (provitamin D2); hexamethyl-Co a Co b-dicyano-7-de(carboxymethyl)-7,8-didehydro-cobyrinate (Pyrocobester); pyrocobester; and vitamin D3.

Exemplary xanthene dyes include Eosin B (4',5'-dibromo, 2',7'-dinitro-fluorescein, dianion); eosin Y; eosin Y (2',4',5',7'-tetrabromo-fluorescein, dianion); eosin (2',4',5',7'-tetrabromo-fluorescein, dianion); eosin (2',4',5',7'-tetrabromo-fluorescein, dianion) methyl ester; eosin (2',4',5',7'-tetrabromo-fluorescein, monoanion)p-isopropylbenzyl ester; eosin derivative (2',7'-dibromo-fluorescein, dianion); eosin derivative (4',5'-dibromo-fluorescein, dianion); eosin derivative (2',7'-dichloro-fluorescein, dianion); eosin derivative (4',5'-dichloro-fluorescein, dianion); eosin derivative (2',7'-diiodo-fluorescein, dianion); eosin derivative (4',5'-diiodo-fluorescein, dianion); eosin derivative (tribromo-fluorescein, dianion); eosin derivative (2',4',5',7'-tetrachloro-fluorescein, dianion); eosin; eosin dicetylpyridinium chloride ion pair; erythrosin B (2',4',5',7'-tetraiodo-fluorescein, dianion); erythrosin; erythrosin dianion; erythrosin B; fluorescein; fluorescein dianion; phloxin B (2',4',5',7'-tetrabromo-3,4,5,6-tetrachloro-fluorescein, dianion); phloxin B (tetrachloro-tetrabromo-fluorescein); phloxine B; rose bengal (3,4,5,6-tetrachloro-2',4',5',7'-tetraiodofluorescein, dianion); rose bengal; rose bengal dianion; rose bengal O-methyl-methyl-ester; rose bengal 6'-O-acetyl ethyl ester; rose bengal benzyl ester diphenyl-diiodonium salt; rose bengal benzyl ester triethylammonium salt; rose bengal benzyl ester, 2,4,6,-triphenylpyrilium salt; rose bengal benzyl ester, benzyltriphenyl-phosphonium salt; rose bengal benzyl ester, benzyltriphenyl phosphonium salt; rose bengal benzyl ester, diphenyl-iodonium salt; rose bengal benzyl ester, diphenyl-methylsulfonium salt; rose bengal benzyl ester, diphenyl-methyl-sulfonium salt; rose bengal benzyl ester, triethyl-ammonium salt; rose bengal benzyl ester, triphenyl pyrilium; rose bengal bis (triethyl-ammonium)salt) (3,4,5,6-tetrachloro-2',4',5',7'-tetraiodofluorescein, bis(triethyl-ammonium salt); rose bengal bis(triethyl-ammonium)salt; rose bengal bis(benzyl-triphenyl-phosphonium)salt (3,4,5,6-tetrachloro-2',4',5',7'-tetraiodofluorescein, bis(benzyl-triphenyl-phosphonium)salt); rose bengal bis(diphenyl-iodonium)salt (3,4,5,6-tetrachloro-2',4',5',7'-tetraiodofluorescein, bis(diphenyl-iodonium)salt); rose bengal di-cetyl-pyridinium chloride ion pair; rose bengal ethyl ester triethyl ammonium salt; rose bengal ethyl ester triethyl ammonium salt; rose bengal ethyl ester; rose bengal methyl ester; rose bengal octyl ester tri-n-butyl-ammonium salt RB; rose bengal, 6'-O-acetyl-, and ethyl ester.

In one embodiment the preferred compounds for formulating are the highly hydrophobic tetrapyrrolic A and B-ring compounds, such as BPD-DA, -DB, -MA, and -MB. Most preferred are the B-ring compounds, BPD-MB, B-EA6, B-B3; the A-ring compounds BPD-MA, A-EA6 and A-B3; and dihydroxychlorins.

These compounds are porphyrin derivatives obtained by reacting a porphyrin nucleus with an alkyne in a Diels-Alder type reaction to obtain a monohydrobenzoporphyrin, and they are described in detail in the issued U.S. Pat. No. 5,171,749, which is hereby incorporated in its entirety by reference. Of course, combinations of photosensitizers may also be used. It is preferred that the absorption spectrum of the photosensitizer be in the visible range, typically between 350 nm and 1200 nm, more preferably between 400-900 nm, and even more preferably between 600-900 nm.

BPD-MA is described, for example, in U.S. Pat. No. 5,171,749; EA6 and B3 are described in U.S. Ser. Nos. 09/088,524 and 08/918,840, respectively, all of which are incorporated herein by reference. Preferred green porphyrins have the basic structure:

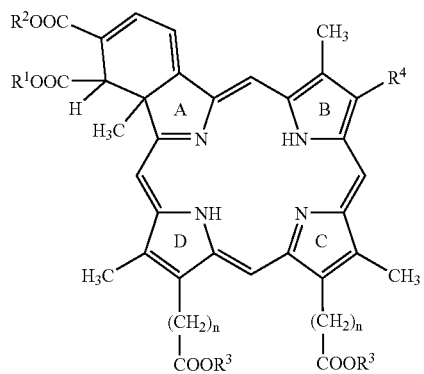

1

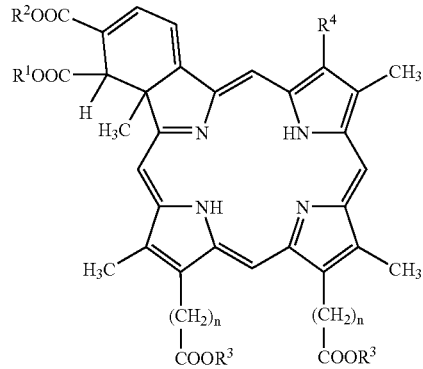

3 or

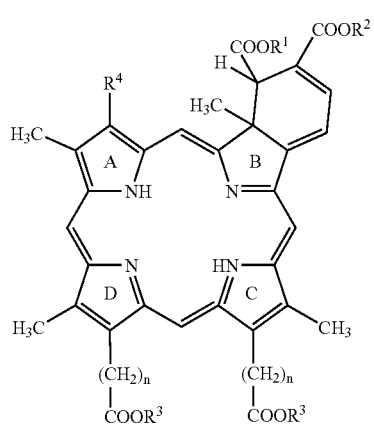

2

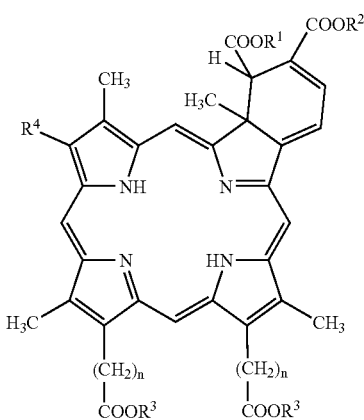

4 where $R^4$ is vinyl or 1-hydroxyethyl and $R^1$, $R^2$, and $R^3$ are H or alkyl or substituted alkyl.

BPD-MA has the structure shown in formula 1 wherein $R^1$ and $R^2$ are methyl, $R^4$ is vinyl and one of $R^3$ is H and the other is methyl. EA6 is of formula 2 wherein $R^1$ and $R^2$ are methyl and both $R^3$ are 2-hydroxyethyl (i.e., the ethylene glycol esters). B3 is of formula 2 wherein $R^1$ is methyl, $R^2$ is H, and both $R^3$ are methyl. In both EA6 and B3, $R^4$ is also vinyl.

The representations of BPD-MA$_C$ and BPD-MA$_D$, which are the components of Verteporfin, as well as illustrations of A and B ring forms of EA6 and B3, are as follows:

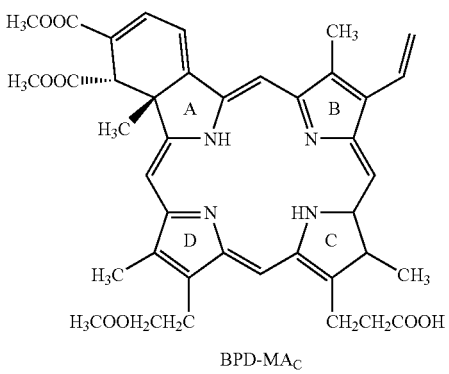

BPD-MA$_C$

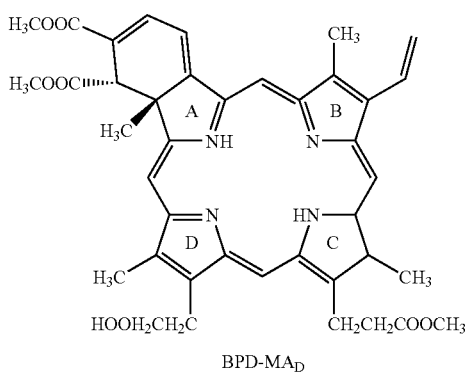

BPD-MA$_D$

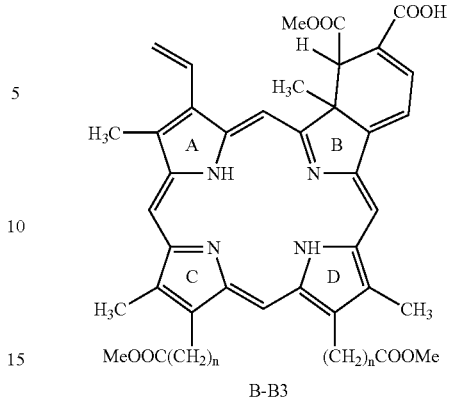

B-B3

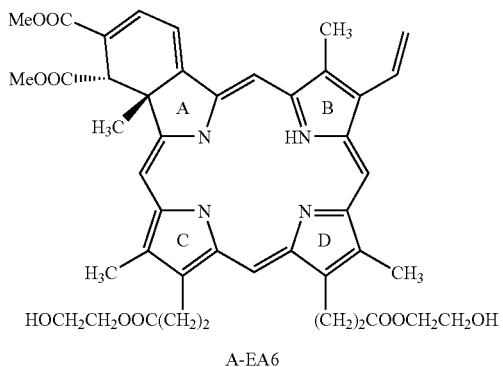

A-EA6

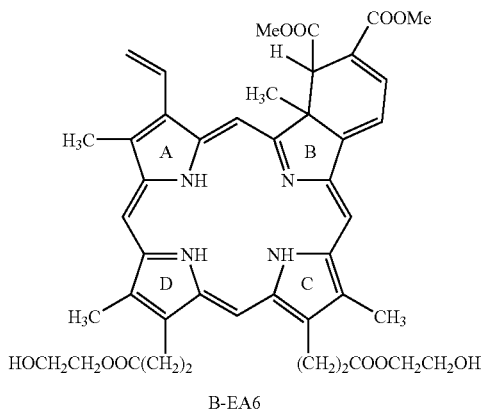

B-EA6

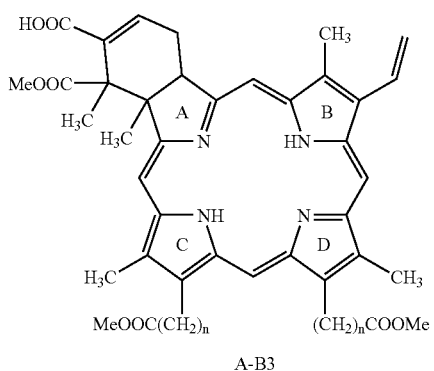

A-B3

Related compounds of formulas 3 and 4 are also useful; in general, $R^4$ will be vinyl or 1-hydroxyethyl and $R^1$, $R^2$, and $R^3$ are H or alkyl or substituted alkyl.

Optionally excluded from inclusion as a photosensitizer of the invention, however, is 5,10,15,20 tetrakis phenyl porphyrin.

Dimeric forms of the green porphyrin and dimeric or multimeric forms of green porphyrin/porphyrin combinations may also be used. The dimers and oligomeric compounds of the invention can be prepared using reactions analogous to those for dimerization and oligomerization of porphyrins per se. The green porphyrins or green porphyrin/porphyrin linkages can be made directly, or porphyrins may be coupled, followed by a Diels-Alder reaction of either or both terminal porphyrins to convert them to the corresponding green porphyrins.

Other non-limiting examples of photosensitizers which may be useful in the invention are photosensitizing Diels-Alder porphyrin derivatives, described in U.S. Pat. No. 5,308,608; porphyrin-like compounds, described in U.S. Pat. Nos. 5,405,957, 5,512,675, and 5,726,304; bacteriochlorophyll-A derivatives described in U.S. Pat. Nos. 5,171,741 and 5,173,504; chlorins, isobacteriochlorins and bacteriochlorins, as described in U.S. Pat. No. 5,831,088; meso-monoiodo-substituted and meso substituted tripyrrane, described in U.S. Pat. No. 5,831,088; polypyrrolic macrocycles from meso-substituted tripyrrane compounds, described in U.S. Pat. Nos. 5,703,230, 5,883,246, and 5,919,923; and ethylene glycol esters, described in U.S. Pat. No. 5,929,105. All of the patents cited in this paragraph are hereby incorporated by reference as if fully set forth. Generally any hydrophobic or hydrophilic photosensitizers, which absorb in the ultra-violet, visible and infra-red spectroscopic ranges would be useful for practicing this invention.

Presently a number of photosensitizer drugs of interest are hydrophobic with a tetrapyrrole-based structure. These drugs have an inherent tendency to aggregate, which can severely curtail photosensitization processes (Siggel et al. J. Phys. Chem. 100(12):2070-2075, December 1996). For example, the synthetic pathway for BPD yields A and B ring intermediates in approximately equimolar quantities, which can be derivatized further. It was found that the A-ring derivatives, such as BPD-MA (Verteporfin), could easily be formulated for delivery using traditional means, whereas B-ring compounds proved more difficult to formulate due to their tendency to undergo self-association.

In an additional aspect of the invention, the photosensitizers of the invention may be conjugated to various ligands that facilitate targeting to tissues and cells before the photosensitizers are formulated with block copolymers. These ligands include those that are receptor-specific as well as immunoglobulins and fragments thereof. Preferred ligands include antibodies in general and monoclonal antibodies, as well as immunologically reactive fragments thereof. Moreover, the block copolymer may be conjugated to the ligands to which the photosensitizer binds to facilitate improved complexing of non-hydrophobic photosensitizers with the copolymer.

B. Block Copolymers

The formulations of the invention may be practiced with a variety of carrier agents, including combinations of such agents. The preferred carrier agents of the invention are symmetric and asymmetric block copolymers composed of two or more blocks. These can be amphiphilic random, graft, or block copolymers, either branched or linear which can be biodegradable or otherwise excretable. The hydrophobe is the part of the copolymer that can interact with the photosensitizer. Examples include, but are not limited to, homo- or hetero-polymers composed of amino acids such as tryptophan, histidine, aspartate, or phenylalanine; pyridines, purines, or indoles; toluene, benzene and alkyl benzene, anthracene, or phenanthrene; and propylene glycol. The hydrophile can be selected from, but is not limited to, any of the following: polyethylene glycol, polyethylene oxide, poly amino acids, polycarboxylates and polysulphonates. Blocks and/or monomers within the blocks are linked by, but not limited to groups such as —CH2-, —O—, —NH—, carbonyl, ester, amide and imine linkages. More preferred are the symmetric and asymmetric block polymers of the structure A-B-A and A-B-A', respectively, where the ratio of hydrophilic to hydrophobic groups range from 1:20 to 20:1. Most preferred are those that can form micellar/mixed micelle suspensions, emulsions, gels or other stable complexes with the photosensitizer of interest. Additional carriers of the invention include lipid-containing compounds capable of forming or being associated with liposomes.

Where block copolymers are used, the copolymers are preferably water-soluble triblock copolymers of composed of polyethylene oxide (PEO), and polypropylene oxide (PPO) denoted as PEO-PPO-PEO or (EO)n1 (PO)m(EO)n2 or HO(C2H4O)a(C3H6O)b(C2H4O)cH (Schmolka, Supra; Alexandridis & Hatton, Colloids and Surfaces 96:1-46, 1995). More preferred are those where a and c are independently from 1-150 units and b ranges from 10-200 units with the overall molecular weight ranging from 1,000 to 50,000 daltons. Particularly preferred are those where a equals c and b ranges from 10-200 units.

Others examples of block copolymers that are useful for this invention are those where the central block is composed of other amphiphilic, charged or uncharged monomeric groups which are likely to interact more specifically with a photosensitizer of interest (Kataoka et al. J. Controlled Release 24:119-132, 1993). These moieties are selected depending on the properties (polarity, charge, aromatic character, etc.) of the photosensitizer to be formulated.

Block copolymers that would be useful in this invention are of the non-toxic di-block, symmetric and non-symmetric tri-block copolymers and dendrimer types. More preferable are the symmetrical triblock copolymers, preferably those composed of PEO-PPO-PEO types of block copolymers, where the hydrophobic PPO provides the methyl groups that are believed to interact with and stabilize the substance to be solubilized.

PEO confers water solubility to the copolymer, although the hydrogen bonding interactions of the ether oxygen with water molecules probably occurs along the entire copolymer. These copolymers are available from a number of commercial sources such as BASF Corporation (Pluronic® series) and ICI (Synperonic® series). In the numeric naming system for both the series, the last digit of the copolymer number multiplied by 10 gives the approximate percent molecular weight of the hydrophilic blocks (PEO). Poloxamers can be roughly divided into 3 main categories, all of which can be useful for stabilizing and delivery of drug substances, namely emulsion forming, micelle forming, and water soluble ones which form an extended network in solution. At higher concentrations they have a tendency to undergo gel formation under certain temperature conditions (Edsman et al. Eur J Pharm Sci. 6, 105-112, 1998). Some of the important factors which determine poloxamer characteristics and behavior in aqueous suspension are the molecular weight, PPO:PEO ratio, temperature conditions, concentration, and presence of ionic materials. There is consequently a wide range of characteristics in existing commercially available copolymers, which can be exploited for formulation purposes, whether for merely monomerization of hydrophobic photosensitizers or for controlled drug delivery purposes. Additionally, alternative PEO-PPO-PEO polymers can be tailored according to requirements of a particular drug substance e.g. molecular weight, PPO:PEO ratio, as well as administration route.

Another characteristic of the copolymers is their wetting or detergent capacity which has been used to promote plasma membrane permeability of various drugs (Melik-Nubarov et al., FEBS Lett. 5; 446(1):194-198, 1999), and thereby increasing bioavailability of the drugs. It has been shown that these copolymers can also act as immunoadjuvants (Hunter et al. Aids Research and Human Retroviruses 10 (Supplement 2): S95-S98, 1994) and could improve the benefits of a regime, for example if used in conjunction with PDT particularly for autoimmune disorders.

The present invention includes the observation that block copolymers form simple complexes with photosensitizing drugs. The type of complexes formed was found to be codependent on the specific block copolymer and the specific photosensitizer utilized. These complexes may be in forms such as micellar, emulsion, gel, matrix or transition phases between the defined states.

Another observation of the invention is that certain copolymers in the poloxamer series spontaneously form micelles with the photosensitizer drug. Micellar formulations have been produced in the laboratory scale using the thin film method. For large scale drug production, the drug-copolymer and other components can be combined using techniques such as, but not limited to, spray or freeze drying, or the Wurster-type coating process (Wurster, J. Amer. Pharm. Assoc. 48:451, 1959) to form granules which will provide a higher surface area for hydration or reconstitution. When forming micelles, it is preferred that block copolymers of the above formula with a=60-80 and b=10 to 40 units in length are used.

The invention also revealed that certain copolymers in the poloxamer series spontaneously form a simple, stable bicomponent oil in water (O/W) emulsions on simply hand-shaking with water or osmotically balanced aqueous solutions. The emulsion particle size in these preparations is small enough for intravenous administration (filterable through 0.2 (m filtration membranes), and particle size is retained over 76 hours without any loss of drug on filtration. This, in conjunction with the knowledge that emulsions can be stabilized as reconstitutable solid state preparations, makes the preparations highly viable as formulations for hydrophobic photosensitizing drugs.

Drugs could be incorporated directly into the block copolymer as described in the Example section, or using minimal amounts of an injectable solvent. Direct dissolution of photosensitizers in poloxamers, particularly those in semi-solid or liquid form at ambient or body temperatures, would also provide useful ointments for topical and mucosal applications. Alternatively, drug dissolved in minimal amounts of a non-toxic solvent may be added to an aqueous suspension of the block copolymer if it does not interfere with drug-copolymer interactions, or destabilize the formulation in any other way.

Further, gel and matrix forming copolymers have been useful for controlled or sustained release, as well as delivery systems that can be triggered, and are prepared at higher polymer concentrations than those deemed suitable for parenteral formulations. Gelling of block copolymers at temperatures above ambient has been exploited in order to form a higher viscosity drug release reservoir in contact with the lesion, either topically or onto mucosal area be treated. This allows a relatively non-invasive spraying of medicament onto affected areas, with good contact maintained between the lesion to be treated and the drug formulation prior to light exposure.

The preferred block copolymers are those that can form stable complexes with a photosensitizer drug of interest. The more preferred copolymers are the ones that form stable emulsions and/or micelles with the photosensitizers, or undergo gel formation at body temperature. Other preferred copolymers are liquefied to permit a medicament, such as a photosensitizer, to be dissolved directly in the absence of a solvent. Poloxamers in liquid form act as highly effective solvents in which hydrophobic drugs can be directly dissolved. Examples 2 and 3 below illustrate this embodiment of the invention by demonstrating that different types of hydrophobic photosensitizers such as BPD-MA and B-B3 can be dissolved in liquefied poloxamers.

Surprisingly, it appears that the nature of the drug can also influence the characteristics of the block copolymer in aqueous solution. Block copolymers tested independently of the drug gave more viscous solutions than in the presence of the drug substance. Without being bound by theory, the reason for this observation may be due to earlier induction or promotion of micelle formation by hydrophobic interactions of the drug substance with the PPO block in the case of poloxamer. Depending on the nature of the active material, its interaction with the block copolymer might alter formulation characteristics e.g. serve to enhance formulation stability by promoting micellization or altering emulsion characteristics. It is now generally accepted that certain block copolymers do, form micelles in aqueous suspensions under certain conditions (Alexandridis et al. Macromolecules 27:2414-2425, 1994).

For parenteral administration the most preferred block copolymers are those that form micelles with the photosensitive compound in the formulation. Water-soluble drugs might also benefit from the presence of hydrophilic polymers to prevent chemical degradation, e.g. hydrolysis (Collett et al. J. Pharm. Pharmacol. 31 (suppl.) P80, 1979) during the manufacturing process, or storage, or improved ease of reconstitution in the clinic.

More preferred for parenteral micellar formulations of highly hydrophobic drugs are the family of poloxamers with the highest commercially available molecular weight of PPO (n=60-80), and those with % PEO in the 20-40% range. For more water soluble formulations, non-micelle forming, hydrophilic polymers from the entire range could be utilized (PEO=40-90%). Emulsion forming polymers (% PEO=10-20%) might be useful for certain hydrophobic and amphiphilic drugs. Poloxamers are non-hygroscopic with water content of less than 0.5% w/w on exposure to the atmosphere. Gel formation takes place in aqueous solutions in the higher molecular weight polymers and is concentration and temperature dependent. For instance, Pluronic® P123 gels at concentrations greater than 20% w/v at ambient temperature conditions. Gelling or viscosity is enhanced at body temperature, which could prove useful for prolonging contact time of topical ocular and enteral formulations with the lesions to be treated using PDT.

As an illustration of one embodiment of the invention, the block copolymer poloxamer series and in particular P123 has been extensively examined. Therefore any poloxamers or block copolymer, in general, that has similar characteristics, as P123 would be useful in this invention. Preferably, the block copolymers are effective in the concentration range of 0.005% to 20% w/v, more preferably in the range of 2 to 20% w/v for parenteral formulations, and 0-100% for topical, enteral and ocular formulations. Poloxarners in liquid form act as highly effective solvents in which hydrophobic drugs can be directly dissolved. Poloxamers in liquid or paste form at ambient temperatures can be employed as liquids or ointments for application P123 has been shown to be highly effective for formulating a range of tetrapyrrolic hydrophobic drug substances, such as the A, B, C and D ring compounds. In the Example section below, formulation of the following A-ring compounds: BPD-MA, A-EA6, A-B3; B-ring compounds; B-EA6, and B-B3; and other photosensitizers such as dihydroxychlorins and pyropheophorbides, with P123 illustrate the versatility of this particular block copolymer. This includes A-ring compounds such as BPD-MA where block copolymers could be used to formulate an alternative product to a concentration as high as 4 mg/ml in 10% P123, and also A-EA6 and A-B3, all of which formulate very readily. B-ring compounds have lower drug loading characteristics, but concentrations of approximately 1.8 mg/ml are typical for B-B3, and lower for B-EA6. A wide range of other compounds e.g. pyropheophorbides and various dihydroxychlorins also formulate with ease to give final formulations at 2 mg/ml in 10% P123 in non-optimized systems. Therefore both the drug loading, and stability could be improved further by adjustments to composition, pH, and/or methodology of formulation. Surprisingly, with BPD-MA, greater drug loading was achieved in formulations with P123 than with any other tested poloxamer. This was also borne out with B-ring compounds, which were the most stable in P123 than in any of the other tested poloxamers, under the given conditions.

Preferred poloxamers of the invention include poloxamer 403 (P123), poloxamer 407 (P127), poloxamer 402 (P122), poloxamer 181 (L61), poloxamer 401 (L121), poloxamer 185 (P65), and poloxamer 338 (F108).

In another embodiment it is preferred that the molar ratio of the copolymer to drug be equal to or greater than one. The present invention includes the discovery that increased ratios of copolymer to drug improves drug "loading" into the disclosed medicament and carrier, or medicament and carrier and solid support, formulations.

In one embodiment of the invention, blends of block copolymers with other ionic and non-ionic surfactants, and other materials may be used to supplement, or compensate for physical and chemical properties lacking in the primary copolymer. For instance, the "oiliness" or difficult hydration of a certain copolymers may be counteracted by inclusion of one or more hydrophilic copolymer(s) or other surfactant families such as, but not limited to PEG, PVP, Triton, Tween, or amphiphilic substances such as bile salts and lipids or lipid derivatives. As an illustration of this embodiment, blending Pluronic®F127 and P123 is demonstrated in Example 15 below. This example also illustrates that blending poloxamers of different characteristics improves subsequent hydration and stabilizes the formulation compared to single poloxamer. Thus specific blends of block copolymers are contemplated for use in the invention in combination with medicaments in general, and photosensitizers in particular.

Mixed micelle systems have been shown to be highly effective in drug stabilization (Krishna et al. Journal 52, 6, 331-336, 1998). Micelles composed of hydrophobic drug-hydrophobic copolymer might be stabilized in aqueous suspension upon addition of one or more hydrophilic copolymer(s), or other surfactant families such as, but not limited to PEG, PVP, Triton and Tween. Ionic surfactants could be envisaged to embed themselves into the hydrophobic micelle with the hydratable headgroup providing high charge density at the micelle water interface. A similar effect might be achieved by blending block copolymers with a low molecular weight, highly water-soluble block copolymer or other surfactant material but not limited to bile salts and their derivatives, fatty acid derivatives, amino acids or other charged head groups. In another embodiment of the invention, photosensitizers can be formulated in mixed micelle systems of ionic and non-ionic polymers. Mixed micelles have been shown to effect drug stabilization (Chow & Bernard, J. Pharm Sci, 70, 8, 924-926, 1980, Krishna et al. Journal 52, 6, 331-336, 1998).

In yet another embodiment, photosensitizers can be formulated as simple oil in water (O/W) emulsions or W/O/W emulsions for formulation of photosensitizers using block copolymers. Certain poloxamers e.g., Pluronic® L61, L121, L122 spontaneously form emulsions in the absence of emulsifiers, or other stabilizing additives. Additionally, formulations of L122 can be filtered through 0.2 μm sterilization filters with no loss of drug, and therefore suggesting a very small particle size. These emulsions have been found to be stable over several days (see Table 3 below). In an additional embodiment, hydrophobic copolymers with and without photosensitizers could be used as an adjunct to PDT, to improve the therapeutic index of the PDT treatment in their capacity as immunoadjuvants, e.g. in the treatment of metastatic lesions, disperse tumors or inflammatory lesions with microbial or autoimmune involvement.

In a further embodiment, the gelling properties of block copolymers can be utilized for preparing ocular formulations. Photosensitizing drugs can be formulated in block copolymer for eye drops for ocular lesions to be treated; for example, hypervascularised areas in macular degeneration, those induced by irritants e.g. excessive exposure to UV. On account of the detergency and surfactant properties, intraocular formulations of photosensitizers in poloxamers (or post PDT washes) would aid in clearing away of cellular debris generated following localized PDT e.g. for glaucoma and other conditions.

Moreover, topical and mucosal copolymer formulated preparations are applicable, but not limited to, mucoadhesive preparations for inflammatory and autoimmune disorders for example, inflammatory bowel disease alopecia, psoriatic lesions.

In another embodiment the surfactant properties of copolymer formulations could be exploited to enhance dermal penetration of photosensitizing drugs, or that of psoriatic and other lesions. Penetration of the blood brain barrier by poloxamers has also been documented and could prove beneficial in the PDT treatment of brain tumors or other disorders. (See Kabanov et al., J. Contr Rel. 22, 141-158, 1998).

In yet another embodiment, cellular uptake of photosensitizers can be accelerated using copolymer formulations. The applicants have shown in Example 11 below that cellular uptake of photosensitizers is accelerated by utilizing poloxamer formulations.

In a further embodiment the copolymer formulations can be used to induce the permeabilization of cellular membranes of the photosensitizers. Cellular internalization of the drug and its intracellular localization is critical in determining the final outcome of PDT. The wetting capacity of copolymers to induce permeabilization of cellular membranes could be exploited using compositions either with or without photosensitizers.

Parenteral administration of block copolymers would be useful in treating all the disorders mentioned above, particularly where treatment or elimination of microvasculature is required. The advantage with poloxamers is that it can be used to formulate highly hydrophobic photosensitizer drugs. Poloxamers have been found to be useful in the invention for formulation of hydrophobic photosensitizer drugs because of their high solubility in both aqueous systems and volatile solvents in which hydrophobic compounds such as BPD-derivatives display good solubility.

In another embodiment administration of block copolymer formulation of photosensitizers could be used for the treatment of various types of cancers. Example 29 illustrates reduction of tumor recurrence in tumor mice model, which were treated with poloxamer photosensitizer formulation. In a further embodiment block copolymers allows both a greater proportion of the medicament to target tissues compared to other formulations. This is illustrated in Example 29 where poloxamer formulations were compared to liposomal formulations using a mice tumor models Preferably, solvents used in the invention when medicaments or photosensitizers are not dissolved into a liquefied carrier, include any organic volatile solvent or mixture of solvents that are capable of dissolving the carrier and photosensitizer. The choice of solvent to use is based in part on the hydrophobicity of photosensitizers and type of carriers, and the choice can be readily made, or made upon routine experimentation, by the skilled artisan. Exemplary solvents used to illustrate this invention include, but are not limited to, methylene dichloride and ethanol.

The following processes can be used for formulations in the absence, and even the presence, of a solid support. Depending on the state of the medicament-carrier mixture and whether the medicament is labile, there are a number of ways of removing the fluids that may be present in the formulation mixture. Spray-drying techniques can be used for medicament-carrier that is in a liquid (molten or in solution) state. For block copolymers that revert to solid state on cooling, the spray dried product can be further micronized or ground to increase the surface area for hydration. Wurster-type technology can be used for semi-solid block copolymers to envelope or coat using exo-support, like a sugar, to prevent agglomeration of the spray dried particles. Supercritical fluid process is a single step process that can accomplish removal of fluids (solvents) from a mixture and results in granules. The granules produced by this process are generally highly porous and result in rapid hydration. This process can be used for medicament and carrier mixture. Supercritical fluid using $CO_2$ has been used for preparing polymeric microparticles and the advantages over other methods have been discussed by Bodmeier et al. (Pharm. Res. 12 (8): 1211-1218, 1995). It is highly preferred that supercritical fluids be used for forming granules for both liquid and solid block copolymers.

The solid product from the above processes can be subsequently hydrated or combined with alternative formulations depending on the mode of application or usage for instance, mixing with ointment bases for topical applications.

Hydration of the medicament carrier with or without the support may be accomplished by addition of an aqueous based solution. The choice of aqueous solution may depend on the components of the formulation mixture and how the hydrated complex is to be used. The aqueous based solution may be water or buffer, which may or may not contain various excipients or stabilizers. The hydrated complex can be processed further if required, or lyophilized or otherwise desiccated for storage. The formulation may be prepared under Good Manufacturing Procedures (GMP). If the components are not sterile, the formulation may be sterilized by any known method in the art. These include heat, filter, radiation, and sterilization under conditions suitable for the medicament-carrier mixture.

C. Solid Supports

The supports useful in the invention include both endo- and exo-supports that permit improved hydration in comparison to medicament-carrier formulations prepared without such supports. The role of the support is to maintain the precursor medicament and carrier formulation in a dry state prior to hydration and use. The support is preferably chosen so that it does not dissolve in the carrier or solvent used to dissolve the medicament. Endo-supports are defined as any support that can be used for depositing the medicament and carrier on the surface of the support and that allows for hydration of the medicament and carrier in an aqueous based medium. An exo-support is defined as any support that partially or wholly coats or encloses or encapsulates the medicament and carrier mixture.

In one embodiment the support that is suitable for this invention are those that are non-toxic, biodegradable, not soluble in organic volatile solvents or carriers used for dissolving the medicament (photosensitizer), suitable for deposition or encapsulation of the mixture, and suitable for hydration of the deposited mixture in an aqueous based medium.

It is preferred that the endo- and exo-support are finely divided and porous such that hydration of the deposited mixture is promoted due to increased surface area.

In one embodiment the endo-support material is soluble upon hydration of the deposited medicament (or photosensitizer) and carrier mixture. Preferred endo-support material include, but are not limited to, ionic salts, lactose, dextrose, sucrose, trehalose, sorbitol, mannitol, xylitol or a naturally occurring polymers and amino acids or derivatives thereof. The more preferred material is lactose and the most preferred is trehalose, which may function both as a solid support and a hydration aid for a medicament/carrier mixture. These embodiments are illustrated in Examples 16 to 20 below, which show the use of such endo-supports for depositing formulations of photosensitizer and one or blend of block copolymer carriers. For illustration purposes the photosensitizers tested were the A and B-ring tetrapyrroles, the carriers were non-blended and blended block copolymers from the poloxamer group and the endo-support were the hydratable sugars such as lactose or trehalose.

Blended poloxamers with dissolvable solid-supports were found to hydrate faster than blended poloxamers without the solid-support. Examples 17 to 20 below demonstrate the use of blended poloxamers P123 and F127 with hydratable solid-supports lactose or trehalose.

In another embodiment the solid-support can be of material that is insoluble in liquefied carrier, solvent, or aqueous based solution but allows for hydration of the deposited mixture from the surface of the solid-support. In the latter case the solid-support material is preferably non-toxic, biodegradable and/or easily removed from the hydrated formulation. Such materials include any be any polymeric material that has been found to be suitable for therapeutic use or implants.

As stated above, solvent removal may be by any process that does not damage the drug and removes the solvent from the block copolymer-photosensitizer drug mixture deposited on the solid-support. Examples of such processes include, but are not limited to, heat drying, microfluidization, spray-drying, Wurster technology, lyophilization, and the use of super critical fluid granulation.

Additional discussion of solid supports for photosensitizer formulations is provided in the simultaneously filed U.S. Patent Application entitled "Supports for Photosensitizer Formulations" which is hereby incorporated by reference in its entirety, as if fully set forth.

D. Pharmaceutical Compositions and Administration

The photosensitizer is formulated into a pharmaceutical composition by mixing the medicament (or photosensitizing agent) with one or more physiologically acceptable carriers, i.e., carriers that are non-toxic to recipients at the dosages, concentrations and modes of administrations employed. The medicament may be used in its solid form or dissolved in an appropriate solvent for addition to the carrier (solid or liquefied) or dissolved in an appropriate solvent. Preferred mixtures should be in appropriate solvents for dissolving both medicament and carrier, and at the desired degree of medicament purity. It is preferred that upon hydration, at the appropriate pH for the medicament, the photosensitizer and carrier form a complex which facilitates delivery of the photosensitizer to the target. Other additives and pharmaceutical excipients can also be added, during or after formulation, to improve the ease of formulation, formulation stability, speed of reconstitution, delivery of the formulation. These include, but are not limited to, penetration enhancers, targeting aids, anti-oxidants, preservatives, buffers, stabilizers, solid support materials. The composition may include osmoregulators if required, such as but not limited to, physiologically buffered saline (PBS), carbohydrate solution such as lactose, trehalose, higher polysaccharides, or other injectable material. A wide variety of excipients and stabilizers are known in the art and their use will depend on the formulation type and application requirements. The function of stabilizers is to provide increased storage stability in cases where the photosensitizer or carriers are labile to heat, cold, light or oxidants or other physical or chemical agents. Other purpose for stabilizer may be for maintaining photosensitizer and/or carrier in a form appropriate for transport to and uptake at the target site. Depending on the solubility, the excipients or stabilizers may be added either prior to deposition step or after the hydration step.

The formulations of the invention may be incorporated into convenient dosage forms, such as capsules, impregnated wafers, ointments, lotions, inhalers, nebulizers, tablets, or injectable preparations. Preferably, the formulations of the invention are administered systemically, e.g., by injection. When used, injection may be by any known route, preferably intravenous, subcutaneous, intradermal, intramuscular, intracranial or intraperitoneal. Injectables can be prepared in conventional forms, either as solutions or suspensions, solid forms suitable for solution or suspension in liquid prior to injection, or as emulsions. Intravenous preparations can be administered as a bolus injection or by controlled infusion following prior dilution if deemed necessary. Controlled intravenous injection is especially preferred following reconstitution, or dilution of the reconstituted drug substance in a physiologically acceptable aqueous preparation.

Solid or liquid pharmaceutically acceptable carriers may be employed. Solid carriers include starch, lactose, calcium sulfate dihydrate, terra alba, sucrose, talc, gelatin, agar, pectin, acacia, magnesium stearate and stearic acid. Liquid excipients include syrup, peanut oil, olive oil, saline, water, dextrose, glycerol and the like. Similarly, the carrier or diluent may include any prolonged release material. When a liquid carrier is used, the preparation may be in the form of a syrup, elixir, emulsion, soft gelatin capsule, sterile injectable liquid (e.g., a solution), such as an ampoule, or an aqueous or non-aqueous liquid suspension. A summary of such pharmaceutical compositions may be found, for example, in Remington's Pharmaceutical Sciences, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral delivery, including topical, transdermal, mucosal, intravaginal, intranasal, intrabronchial, intracranial, intraocular, intra-aural and rectal administration. The pharmaceutical preparations may also contain minor amounts of nontoxic auxiliary substances such as wetting or emulsifying agents, pH buffering agents and so forth. Pharmaceutical compositions formulated for timed release may also be prepared. The preparations may include osmoregulators if required, such as but not limited to, physiologically buffered saline (PBS), carbohydrate solution such as lactose, trehalose, higher polysaccharides, or other injectable material.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable preparations include, but are not limited to, solution, gels, suspensions, emulsions, creams, ointments, powders, liniments, salves, eye drops, and the like. If desired, these may be sterilized or mixed with auxiliary agents, e.g., preservatives, stabilizers, wetting agents, buffers, penetration enhancers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, preservatives, and/or antioxidants in addition to the compounds of the invention.

For the preferred topical applications, especially for humans, it is preferred to administer an effective amount of the formulation to a target area, e.g., skin surface, mucous membrane, eyes, etc. This amount will generally range from about 0.001 mg to about 1 g per application, depending upon the area to be treated, the severity of the symptoms, and the nature of the topical vehicle employed.

The formulations of the invention may be given in combination with one or more additional compounds that are used to treat the disease or condition. For treating cancer, the formulations are given in combination with anti-tumor agents, such as mitotic inhibitors, e.g., vinblastine; alkylating agents, e.g., cyclophosphamide; folate inhibitors, e.g., methotrexate, pritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical preparations comprising any known cancer therapeutic in combination with the formulations disclosed herein are within the scope of this invention.

The pharmaceutical preparations of the invention may also comprise one or more other medicaments such as anti-infectives including antibacterial, anti-fungal, anti-parasitic, anti-viral, and anti-coccidial agents.

Typical single dosages of the formulations of this invention are between about 1 ng and about 10 g/kg body weight. The dose is preferably between about 0.01 mg and about 1 g/kg body wt. and, most preferably, between about 0.1 mg and about 100 mg/kg body wt. For topical administration, dosages in the range of about 0.01-20% concentration of the compound, preferably 1-5%, are suggested. A total daily dosage in the range of about 1-500 mg is preferred for oral administration. The foregoing ranges are, however, suggestive, as the number of variables in regard to an individual treatment regime is large, and considerable excursions from these recommended values are expected.

Effective amounts or doses of the compound for treating a disease or condition can be determined using recognized in vitro systems or in vivo animal models for the particular disease or condition. In the case of cancer, many art-recognized models are known and are representative of a broad spectrum of human tumors. The compounds may be tested for inhibition of tumor cell growth in culture using standard assays with any of a multitude of tumor cell lines of human or nonhuman animal origin. Many of these approaches, including animal models, are described in detail in Geran, R. I. et al., "Protocols for Screening Chemical Agents and Natural Products Against Animal Tumors and Other Biological Systems (Third Edition)", Canc. Chemother. Reports, Part 3, 3:1-112.

E. Storage & Handling

Poloxamer based formulations do not require extensive precautions (shielding from light and exposure to air (oxygen and moisture) as is often recommended with phospholipids for liposomal formulations, especially in conjunction with photosensitizers. Thus the photosensitizer drug substance would be the only labile material in the poloxamer based formulations, compared to the conventional emulsion or liposomal based formulations, where in addition to the photosensitizer, phospholipids and other labile components would be present.

Poloxamer block copolymer formulations have an extended shelf life because poloxamers are chemically inert molecules with none of the hydrolytic and oxidative/photo-oxidative degradation problems, associated for instance with liposomal systems. Peroxide generation in unsaturated phospholipid systems contributes to propagation of free radical processes, which can potentially degrade not only the lipids themselves, but also the active drug. Free radicals are not expected to be generated in poloxamer systems to the same extent, and the need for additives e.g. anti-oxidants, would be greatly reduced when compared to unsaturated liposomal formulations. Since poloxamers are synthetic, there is also no concern about potential transmission of biohazardous disease vectors associated with animal derived products.

Poloxamer based formulation can be rapidly and easily be developed for highly economic large scale manufacturing procedures. Due to the simplicity and non-fragile nature of the components, manufacturing can be carried out in a single step prior to packaging for reconstitution by spray drying, lyophilizing or low heat drying from a volatile solvent, under conditions for Good Manufacturing Practices (GMP) conditions).

F. Drug Release

In liposomal formulations of BPD-MA, drug fluorescence is concentration quenched due to its location in the liposomal membrane. This allows its release to plasma proteins to be monitored. This is not the case for copolymer formulations lacking fluorescence quenching, in which case it is assumed that the drug is encompassed in its non-aggregated form in a more dynamic micellar system. It is therefore likely to be released instantaneously in the presence of alternative drug-binding molecules (such as lipoproteins) upon injection into the circulation. Example 11 below shows the high level of association of B-ring drugs with the lipoprotein fraction following a very brief exposure to human plasma.

G. Photodynamic Therapy

Preferably, electromagnetic radiation, such as from ultraviolet to visible and infra red light, is delivered after administration of the compositions and formulations of the invention. Also preferred in the invention is the use of low-dose PDT. By "low-dose PDT", it is meant a total photodynamic therapy experience at substantially lower levels of intensity than that ordinarily employed. Generally, there are three significant variables—the concentration of the photosensitizing drug, the intensity of the radiation employed and the time of exposure to light, which determines the total amount of energy ultimately delivered to the target tissue. Generally, an increase in one of these factors permits a decrease in the others.

For example, if it is desired to irradiate only for a short period of time the energy of irradiation or the concentration of the drug may be increased. Conversely, if longer time periods of irradiation are permitted, lower irradiation intensities and lower drug concentrations are desirable. In some instances, the combination of 0.15 mg BPD-MA as a drug concentration and approximately 1 J/cm2 total radiation from an appropriate radiation source provided successful results. The use of low dose PDT offers an additional advantage in the form of reducing the likelihood of PDT side effects such as damage to unintended tissues.

It is understood that the manipulation of these parameters will vary according to the nature of the tissue being treated and the nature of the photosensitizer (PS) employed. However, in general, low-dose PDT employs combinations of the drug concentration, radiation intensity, and total energy values which are several fold lower than those conventionally used for destroying target tissues such as tumors and unwanted neovascularization. One measure might be the product of PS concentration (e.g., in ng/ml)×intensity (e.g., in mW/cm2)×time (e.g., in seconds). However, it is difficult to set absolute numbers for this product since there are constraints on each of the parameters individually. For example, if the intensity is too low, the PS will not be activated consistently; if the intensity is too high, hyperthermic and other damaging effects may occur. Additionally, in some instances, ambient or environmental light available at the target cell or tissue undergoing PDT may be sufficient in the absence of additional deliberate irradiation.

Similarly, PS concentrations cannot vary over any arbitrary range. There may also be constraints on the time during which radiation can be administered. Accordingly, the product of the foregoing equation is only a rough measure. However, this approach may provide a convenient index that can be adjusted according to the relative potency of the PS employed, and in general, an increase in intensity would permit a decrease in time of irradiation, and so forth.

Having now generally described the invention, the same will be more readily understood through reference to the following examples which are provided by way of illustration, and are not intended to be limiting of the present invention, unless specified.

EXAMPLES

The following general comments on materials apply to the following examples, unless otherwise noted.

BPD-MA, BPD derivative EA6, and B3 A and B ring compounds were synthesized as described in the patents recited above. BPD-MA, A-EA6, B-EA6, A-B3, and B-B3 were obtained from QLT PhotoTherpeutics Inc. (Vancouver, B.C., Canada; QLT).

Example 1

Prescreening of Block Copolymers for Photosensitizer Drug Loading

The following example illustrates the pre-screening of block copolymers for utility in drug loading for intravenous delivery by studying the aqueous suspension characteristics.

Although certain block copolymers have been used previously as emulsion stabilizers in various pharmaceutical formulations, block copolymers which themselves emulsify in aqueous suspension have not been studied in great detail for parenteral formulations. This has been due to the greater difficulty in controlling and maintaining particle size during manufacture and storage. Ideally, a stable micellar suspension is preferred. For extended shelf life, the final formulation is required to be in a dry form which is easily reconstituted for injection. An acceptable minimum reconstituted drug concentration for an intravenous formulation is in the range of 1-2 mg/ml with at least 4 h post reconstitution stability in aqueous suspension. Important considerations for intravenous formulation are (i) delivery of drug in a non-aggregated form, (ii) low viscosity preparations (iii) non-frothy preparations, and (iv) sterile filterability prior to drying. A criterion for hydrophobic drug formulation is effective delivery to the plasma lipoproteins, which act as intermediate drug carrier in vivo to tissues displaying high levels of LDL receptors. These include hyperplastic tissues and those undergoing repairs, e.g. under inflammatory conditions.

In this experiment the copolymers were pre-screened for their potential as injectable drug formulation agents, starting with the examination of their aqueous suspension characteristics at various concentrations i.e. whether they formed emulsions or solutions in water. The Pluronic® copolymers used in this and subsequent experiments were obtained from BASF Corp. and are described in the following table with their PPO/PEO contents and molecular weights.

5 ml suspensions of each Pluronic were made at 5%, 10%, 15% and 20% w/v in physiologically buffered saline (PBS), pH 7.4. This was facilitated by sonicating the suspensions in a water bath (Aquasonic, 250D, VWR Scientific) at 55° C. The suspensions were then examined and the viscosity of each suspension was determined visually by the thickness of film left on vial wall as it was tilted, and by relative ease of filtration through 0.2 µm filters (Sterile Acrodisc 13, Gelman Sciences).

TABLE 1

| Poloxamer[1] | Pluronic ®[2] | PEO[7] (a) | PPO[8] (b) | MW (g/mol) |
|---|---|---|---|---|
| 401 | L[3]121 | 6 | 67 | 4400 |
| 402 | L122 | 13 | 67 | 5000 |
| 403 | P[4]123 | 21 | 67 | 5750 |
| 407 | F[5]127[6] | 98 | 67 | 12000 |
| 338 | F108[6] | 128 | 54 | 15000 |
| 181 | L61 | 3 | 30 | 2000 |
| 185 | P65 | 19 | 30 | 3400 |
| 188 | F68[6] | 75 | 30 | 8350 |
| 124 | L44[6] | 11 | 21 | 2200 |

[1]Block copolymer Poloxamer No.
[2]Pluronic ® No. (BASF) equivalent to [1] Poloxamer No
[3,4,5]Pluronic No. prefix: L[3]: liquid; P[4]: paste; F[5]: flake
[6]Available in NF grade (from BASF)
[7]PEO: poly(ethylene oxide)
[8]PPO: poly(propylene oxide)

Table 2 summarizes the qualitative results of the solution appearance, viscosity and filterability of 5 to 20% weight by volume (w/v) concentration range of the different type of poloxamers in PBS. Generally, viscosity in both solutions and emulsions increased with Pluronic concentration. Copolymers forming highly viscous suspensions (e.g. preparations at higher Pluronic concentrations) or those forming highly unstable emulsions e.g. L61 were not further tested. Copolymers with a lower PEO content less that 30% (L61, L121, L122)displayed limited water solubility, and tended to form oily emulsions rather than clear solutions. Under the above conditions, Copolymers that formed solutions were those with a higher PEO content such as P123, P127, F68, F108, and were tested further for lower concentrations.

Example 2

Photosensitizer Drug Loading of BPD-MA Using PEO-PPO-PEO Block Copolymers

The following example illustrates the utility of block copolymers for drug loading of an A-ring tetrapyrrolic compound.

In this experiment the use of copolymers for drug loading capability and formulation stability over a 3 day period was examined using the photosensitizer drug BPD-MA. The criteria for choosing the copolymers were based on the solution and viscosity characteristics described in Example 1. The 'melt' method is used for the preparation and screening of the large number of samples and is described as follows. At temperatures above 50° C., poloxamers are in their molten state and serve as excellent solvents for tetrapyrrolic compounds, thus avoiding the need for pre-dissolution of drugs in organic solvents. 5 mg of BPD-MA was dissolved with the aid of vortex mixing and sonication at 55° C. into the polymer 'melts' to give a final concentration of 5% to 20% w/v of the respective Pluronic. To each melt sample, 2.5 ml of PBS was added to give a final BPD-MA concentration of 2 mg/ml. Samples were allowed to equilibrate to room temperature before drug loading was determined at time zero ($T_0$). 1 ml of suspension was removed for centrifugation (Microfuge, 14,000 rpm, 30 min), and the rest filtered through 0.2 µm filters (Millipore). The filtrate was diluted 1:100 in PBS and the absorbance at 690±3 nm determined (uv-vis spectrophotometer Beckman DU-6401). This procedure was repeated 72 hours later following storage at room temperature and the absorbance measurement ($T_{72}$).

TABLE 2

Solubility, viscosity and filterability characteristics of poloxamers

| Pluronic | 5% w/v Appearance/Viscosity | Filtered | 10% w/v Appearance/Viscosity | Filtered | 15% w/v Appearance/Viscosity | Filtered | 20% w/v Appearance/Viscosity | Filtered |
|---|---|---|---|---|---|---|---|---|
| L121 | Opaque emulsion | Yes | Opaque emulsion | Yes | Opaque emulsion | Yes | Gels | No |
| L122 | Frothy emulsion | Yes | Frothy emulsion | Yes | Viscous frothy emulsion | Yes | Gels | No |
| P123 | Clear frothy solution | Yes | Clear frothy solution/ slight viscosity | Yes | Clear frothy solution/ medium viscous | No | Clear frothy solution/ medium viscous | No |
| F127 | Clear solution/low viscosity | Yes | Clear solution/ medium viscosity | Yes | Clear solution/ high viscosity | Yes | Clear solution/ high viscosity | No |
| L61 | Oily emulsion/ low viscosity | No | Oily emulsion/ low viscosity | No | Oily emulsion/ low viscosity | No | Unstable emulsion | No |
| P65 | Frothy solution/low viscosity | Yes | Frothy solution/low viscosity | Yes | frothy solution/low viscosity | Yes | frothy solution/low viscosity | Yes |
| F68 | Clear solution | Yes | Clear solution | Yes | Clear solution | Yes | Slightly viscous | Yes |
| F108 | Clear solution | Yes | Frothy viscous solution | Yes | High viscosity solution | No | High viscosity solution | No |

The following table summarizes the results of the above experiment.

TABLE 3

Absorbance ($A_{693}$) of BPD-MA of filtered (F) and centrifuged (C) samples after hydration.

| Pluronic | C/F[1] | 5% w/v $T_0$ | 5% w/v $T_{72}$ | 10% w/v $T_0$ | 10% w/v $T_{72}$ | 15% w/v $T_0$ | 15% w/v $T_{72}$ | 20% w/v $T_0$ | 20% w/v $T_{72}$ |
|---|---|---|---|---|---|---|---|---|---|
| L122 | C | 0.51 | 0.64 | 0.74 | 0.76 | 0.8 | 0.41 | N/D[2] | N/D |
|  | F | 0.61 | 0.53 | 0.76 | 0.73 | 0.43 | 0.57 | N/D | N/D |
| P123 | C | 0.44 | 0.62 | 0.86 | 0.66 | N/D | N/D | N/D | N/D |
|  | F | 0.64 | 0.66 | 0.69 | 0.58 | N/D | N/D | N/D | N/D |
| F127 | C | 0.74 | 0.64 | 0.67 | 0.67 | 0.81 | 0.88 | N/D | N/D |
|  | F | 0.62 | 0.63 | 0.66 | 0.64 | 0.87 | 0.83 | N/D | N/D |
| P65 | C | 0.1 | 0.02 | 0.43 | 0.36 | 0.9 | 0.73 | 1.0 | 0.97 |
|  | F | 0.02 | 0.09 | 0.35 | 0.43 | 0.81 | 0.78 | 0.97 | 0.97 |
| F68 | C | 0.3 | 0.25 | 0.13 | 0.05 | 0.09 | 0.06 | 0.3 | 0.07 |
|  | F | 0.25 | 0.33 | 0.06 | 0.13 | 0.11 | 0.07 | —?? | 0.24 |
| F108 | C | 0.17 | 0.19 | 0.72 | 0.65 | N/D | N/D | N/D | N/D |
|  | F | 0.59 | 0.58 | 0.68 | 0.73 | N/D | N/D | N/D | N/D |

[1]N/D - Not done

The results show that highest drug loading using 5% w/v copolymers gave $A_{693}$ ranging from 0.5 to 0.7 for L122, P123 and F127 in both centrifuged and filtered preparations. These copolymers have the highest PPO content (67 Units). Drug loading using 10% w/v copolymer showed highest drug loading with L122, P123 and F127 and F108 (PPO 54 units) with $A_{693}$ ranging from 0.58 to 0.76. P65 (PPO 30 units, PEO 19 units) showed minimal incorporation at 5 and 10% w/v but total incorporation at 15 and 20% w/v. Drug loading was greater than in F68 that has the same number of PPO units. Solution forming poloxamers such as P123, L122 and F127, show little discrepancy between centrifuged and filtered samples, suggesting that both procedures were equally effective in removing unincorporated photosensitizer drug aggregates from the formulations. The $A_{690}$ reading were comparable between day 0 and day 3 which implied that there was no loss of stability of BPD-MA formulations in Pluronic following 3 days storage.

Based on the observation that greater drug loading is dependent on lower water solubility (low PEO) within a given PPO group, but without being bound by theory, it seems possible that micelle formation is important for stabilization of highly hydrophobic drug substances. A reason why F68 does not perform well may be because of its high water solubility. The extended PEO chains (PEO 75 units) would not be conducive to micelle formation.

Example 3

Photosensitizer Drug Loading of B-B3 Using Pluronic Block Copolymers

The following example illustrates the utility of block copolymers for drug loading of B-ring tetrapyrrolic compounds, and maintaining the drug in a non-aggregated form.

For this experiment copolymers were examined for drug loading capability and formulation stability over a 24 h period using the drug B-B3. The experimental procedure is the same as described in Example 2 with the following exceptions. The copolymers were tested at 10%, 15% and 20% w/v. For convenience centrifugation rather than filtration was used to eliminate unincorporated drug prior to absorbance measurement. It has previously been observed that aggregates of B-ring compounds have a characteristic red shifted, high extinction absorbance at 730 nm±10 nm, which takes place at the expense of the typical 690 nm absorbance attributed to monomers. The 730 peak correlates with sub-optimal formulation conditions, and has proved useful for evaluation of formulation quality. Dissolution of green crystalline B-ring compounds in melted poloxamers resulted in a reddish brown solution absorbing entirely at 690 nm. Similar color was observed in stable formulations of B-ring compounds in aqueous suspensions of poloxamers.

Table 4 shows results of B-B3 drug loading using various block copolymers. Overall, the results for B3-B drug loading displayed the same general pattern as for BPD-MA as seen in Example 2, but with lower drug loading. Polymers L122, P123 and F127 showed the highest drug loading. Unlike loading of BPD-MA in P65 (Example 2), the drug loading was comparable to the PPO 67 unit group, this was not the case for B-B3, even at the highest P65 concentrations tested.

TABLE 4

Absorbance ($A_{693nm}$) of B-B3 formulation following hydration and centrifugation

| Pluronic ® | 10% w/v $T_0$ | 10% w/v $T_{24}$ | 15% w/v $T_0$ | 15% w/v $T_{24}$ | 20% w/v $T_0$ | 20% w/v $T_{24}$ |
|---|---|---|---|---|---|---|
| L122 | 0.54 | 0.50 | 0.5 | 0.56 | N/D | N/D |
| P123 | 0.52 | 0.53 | N/D | N/D | N/D | N/D |
| F127 | 0.57 | 0.4 | 0.51 | 0.48 | N/D | N/D |
| F108 | 0.1 | 0.015 | N/D | N/D | N/D | N/D |
| P65 | 0.07 | 0.07 | 0.15 | 0.13 | 0.36 | 0.24 |
| F68 | 0.03 | 0.025 | 0.02 | 0.02 | 0.03 | 0.03 |

(n = 2)

On 1:100 dilution, the P123 formulation displays a 690 nm absorbance in PBS which is similar to that in organic solvents e.g. methanol suggesting a similarly hydrophobic environment for the drug in the Pluronic formulation. Twenty minutes following dilution produced a 730 nm peak in the F127 formulation (results not shown), but not in the 10% w/v P123 or L122 formulations. This is again indicative of a micellar organization for the poloxamers in aqueous suspensions, particularly in those with an intermediate PEO content>10% w/w. Highly water soluble polymers such as F127, form unstable preparations particularly on dilution, as the ratio F127:drug decreases resulting in micelle destabilization with consequent drug aggregation.

Centrifugation of unstable formulations (P65, F68, F108) resulted in an aggregated drug pellet absorbing predominantly at 730 nm wavelength, even on suspension in 100% fetal bovine serum. This confirms that the 730 nm peak may indicate low non-aggregated drug bioavailability to plasma lipoproteins and therefore should be avoided in formulation of B-ring compounds.

Example 4

Drug Loading of B-EA6 and B-B3 Using Block Copolymers and Thin Film Approach

The following example describes an alternative method for B-ring hydrophobic drugs (B-B3 and B-EA6) that were previously described as being difficult to formulate, and to do so using smaller quantities of drug and block copolymers. Although the melt method described in Example 2 works well for formulating hydrophobic drugs, it requires constant stirring and vortex mixing to maintain the drug in contact with the small volume of block copolymers used. The smallest volume that could be prepared using such a method was approximately 5 ml. Creating a thin film from a solution of both the drug and Pluronic in a volatile organic solvent on the other hand, allows a larger surface area for faster hydration.

The B-ring drugs B-EA6 and B-B3 were tested by the following formulation method. 5 mg of the drug and 0.5 g Pluronic were dissolved in methylene chloride ($CH_2Cl_2$) and combined to give final volume of 2.5 ml in a round bottom flask. The solvent was removed by rotary evacuation, and the resultant thin film hydrated with 2.5 ml PBS at 50° C. in a sonication bath. After cooling to room temperature (1-2 hours), samples were centrifuged to remove unincorporated drug, and $A_{690}$ of 1:100 dilutions was determined.

The results of formulating B-B3 and B-EA6 by the poloxamer based thin film approach are summarized in Table 5.

TABLE 5

| Pluronic (10%) | Absorbance($A_{690}$) | |
| --- | --- | --- |
|  | B-B3 | B-EA6 |
| P123 | 0.8 | 0.315 |
| L122 | 0.6 | 0.275 |
| F127 | 0.4 | 0.08 |

It was surprising to note that B-EA6 could be formulated with block copolymers because of earlier poor results obtained with other carriers and liposomal formulation attempts. B-B3 was more readily formulated in poloxamers compared to B-EA6 under the above conditions. The order of formulation efficiency remained the same as observed in Example 3, i.e. F123>L122>F127. Both drug preparations in 10% F127 developed the 730 absorbance peak within 15 min of dilution in PBS. This was indicative of formulation destabilization and drug aggregation in aqueous suspensions, perhaps due to an unstable micellar structure.

Example 5

Hydrophobic Photosensitizer Drug Loading Using Block Copolymers

The following example illustrates one embodiment for hydrophobic drug loading using block copolymers.

Unless otherwise stated, the following protocol was used for all subsequent formulation of the photosensitizer drugs in poloxamers:

1 to 2 mg drug and 25-100 mg Pluronic are combined in methylene dichloride ($CH_2Cl_2$) to yield drug concentration of 1 mg/ml. $CH_2Cl_2$ is removed rapidly by rotary evacuation (Rotavapor R-124, Bucchi B172 Vacobox pump) at 50°, at maximum speed of rotation. Once a steady minimum pressure is achieved, the flask is held under vacuum for a further 20-30 min. The resulting thin film is hydrated with 1 ml of physiologically buffered saline (PBS, pH 7.4) or 9.5% w/v lactose, using hand swirling (with glass beads) at 23° C., to give a final drug concentration of 1 or 2 mg/ml, 2.5-10% (w/v) Pluronic as required. Samples are kept overnight at room temperature to allow unincorporated drug to fall out, and then spun at 14,000 rpm {Eppendorff, Microfuge} for 30 min. Supernatant is decanted off into a fresh Eppendorff vial, and diluted 1:100 in the iso-osmolar medium used for thin film hydration (PBS or lactose) for determination of absorbance 690 nm ($A_{690}$). Formulations are stored at 4° C. or frozen at −20° C. for long term storage.

Example 6

Protocol for Liposomal Photosensitizer Drug Formulation

The following example describes a protocol for liposomal preparation of hydrophobic photosensitizers. It is based on existing methodology (Hope et al., Biochim. Biophys. Acta 812, 55-65, 1985).

5 mg drug and lipids (40% EPG in DMPC) are combined in $CH_2Cl_2$ at a drug to lipid ratio of 1:10 w/w in 250 ml round bottom flask. The maximum concentration of drug in solvent is 2 mg/ml. $CH_2Cl_2$ is removed rapidly as described in Example 5. The resulting thin film is hydrated with 2.5 ml lactose solution (9.5% w/v) using hand swirling with glass beads at 40° C. Extrusion using Model 4T (Lipex Biomembranes Inc. B.C., Canada) is carried out with the thermostat set at 40° C. The multilamellar vesicles (MLVs) arising from hydration steps of the liposomal formulation were also examined under the microscope. MLVs are successively extruded 5 times through each of the 400 nm, 200 nm and 100 nm polycarbonate membranes (Nuclepore PC, Costar). Extruded samples were diluted 1:100 in PBS (pH 7.4) and the absorbance determined at 690 nm wavelength.

Example 7

Comparison of Liposomal and Block Copolymer Photosensitizer Formulations

This example demonstrates that micellar formulations of photosensitizers using block copolymers were either comparable or superior to the liposomal formulations.

In this experiment liposomal and block copolymer (micellar) photosensitizer formulations of A- and B-ring compounds of EA6 and B3 were compared. Each of the photosensitizer samples was prepared at a final drug concentration of 2 mg/ml. The block copolymer P123, and the liposomal formulations were prepared as described in the Examples 5 and 6, respectively.

Table 6 shows the results of the photosensitizer drug loading using 10% P123 and liposomes. The A-rings could be formulated using liposomes but formulation of the B-ring compounds was not very efficient. P123 was found not only able to formulate the A-ring compounds but also the B-ring compounds. With the exception of A-B3, the overall results for the drug loading showed that the P123 formulations were either superior or comparable to the liposomal formulation.

TABLE 6

| Drug | Liposome mg/ml | P123[1] mg/ml |
| --- | --- | --- |
| A-EA6 | 0.98 | 1.82 |
| A-B3 | 1.84 | 1.33 |
| B-EA | 0.06 | 0.37 |
| B-B3 | Very low | 1.24 |

[1]Pluronic P123 10% weight/volume

It was observed that in the liposomal formulation the step of hydration of thin film of the A-ring compounds took place readily with the total drug incorporation into MLVs. Microscopic examination did not reveal presence of aggregates. Extrusion took place readily under low pressure without significant loss of drug. In contrast, MLVs arising from hydration of B-ring films were unevenly shaped, with drug aggregates and crystalline structures commonly present. These crystals were problematic because they caused filter blockage during the extrusion process and resulted in significant drug loss. Liposomal formulation with B-ring preparations resulted in very small quantity being incorporated in the liposomes (Table 7).

Formulation with block copolymer P123 resulted in ready hydration of thin films of the A-ring compounds. For the B-ring compounds there was greater drug incorporation using P123 compared to the liposomal formulation.

The above example demonstrates that block copolymer P123 readily incorporated different types of photosensitizers with either similar or superior drug loading compared to the liposomal formulations.

Example 8

Formulation of Dihydroxychlorins in Block Copolymers

The following example illustrates the use of block copolymer for formulating dihydroxychlorin photosensitizers.

In this experiment the following three selected dihydroxychlorins were examined for formulation with 10% P123. Each of the drugs was prepared to a final concentration level of 1 mg/ml and the formulation protocol used is described in Example 5. These compounds were prepared as described in U.S. patent application Ser. Nos. 09/551,159 and 09/551,160, both filed Apr. 14, 2000, and 60/129,324, filed Apr. 14, 1999, all three of which are hereby incorporated by reference as if fully set forth. One of these compounds, JM 4, was further tested for drug incorporation using 2.5 to 10% P123.

TABLE 7

| ID No. | Formula |
|---|---|
| JM3 | T(m-OH)PC = 5,10,15,20-tetra (meta-hydroxyphenyl)-2-3-dihydroxychlorin |
| JM 4 | T (p-Me) PC = 5,10,15,20-tetra (para-methyl phenyl)-2,-3-dihydroxychlorin |
| JM 24 | $H_2DPC(OH)_2$ |

All of the above dihydroxychlorin compounds were formulated with ease using 10% P123. The compounds underwent total incorporation with no pellet formation on centrifugation either directly following formulation or 24 h later. The micelle size ranged from 15 to 20 nm measured by laser light scattering (Submicron Particle Sizer Model 370, NICOMP, Santa Barbara, Calif.). The formulation was also found to be stable following overnight storage.

Table 8 shows the results of drug incorporation using different concentration of the copolymer P123. The readings following overnight storage and centrifugation. Formulation of JM4 at 2 mg/ml showed that the amount of drug incorporated was found to be dependent on the concentration of polymer in the formulation.

TABLE 8

| P123 % w/v | Incorporation mg/ml |
|---|---|
| 2.5 | 0.92 |
| 5 | 1.43 |
| 10 | 2.00 |

The above example demonstrates the versatility of the P123 block copolymer for formulating different types of photosensitizers. Additionally this example shows that the concentration of the block copolymer will dictate the level of photosensitizer incorporation.

Example 9

Plasma Distribution of Photosensitizers Delivered by Block Copolymer and Liposomal Formulations This example illustrates that B-ring photosensitizers formulated with the block copolymer L123 are delivered with the same or greater efficiency to the lipoprotein fraction of the plasma compared to the standard liposomal formulation of an A-ring compound, BPD-MA.

In this experiment liposomal, block copolymer and dimethyl sulfoxide (DMSO) formulations of the B-ring compounds, B-EA6 and B-B3 were examined for their partitioning between the different components of human plasma. BPD-MA liposomal formulation was used as the standard and the DMSO as a control. Pluronic micellar and liposomal formulations of the photosensitizers were prepared as described in Examples 5 and 6, respectively. DMSO formulation was prepared by direct dissolution of the drug in DMSO.

The assay for centrifugal separation of plasma components was based on Rudel *Biochem J.,* 139, 89-95, 1974.) and subsequently modified by Alison et el. *Photochem. Photobiol.* 52(3): 501-507, 1990). It has been scaled down to allow a shorter centrifugation time. Evidence of clear separation and identities of the different layers has been established. MACE (monoaspartyl chlorin e6) is a relatively water soluble photosensitizer known to be bound and transported by albumin in the circulation. The validity of this assay was further tested using MACE, which was found to be overwhelmingly associated with the albumin (87%), with very little in the lipoprotein layer (11%).

Fresh human plasma was collected in EDTA, and KBr added to give a concentration of 1.21-1.23 g/ml. Photosensitizer formulations were added to 0.8 ml pre-warmed plasma (37° C.) to give a final concentration of 10 µg/ml. 30 sec later, plasma was cooled for 15 min on ice, and under layered with 2.45 ml KBr/EDTA at 1.21 g/ml in thick polycarbonate tubes. Samples were centrifuged at 512K g (100,000 RPM, Beckman TLA 100.3 rotor) for 16-18 h at 20° C. Layer positions were marked to allow determination of layer volume. Each layer was sampled by removing a portion using a syringe inserted from the top. Known volumes of plasma layers were removed into TX/PBS in an 1.8 ml tube (Eppendorf Scientific, Inc., Eppendorf) to give a final concentration of 1% TX. Samples were vortex mixed and then spun for 2 min at 14 000 RPM in an Eppendorf centrifuge for clarification. Fluorescence at 690 nm ($\lambda_{ex}$=434 nm) was read alongside standards of known drug concentration. Total drug present in each layer was calculated on the basis of known layer volume and absorbance value.

Tables 9 and 10 show the percentage distribution of B-B3 and B-EA6, in the various components of the fractionated plasma in comparison to BPD-MA, using liposomal, copolymer and DMSO formulations.

As expected from previous studied liposomal BPD-MA associated predominantly with the lipoproteins (Tables 9 and 10). Comparable results were obtained for the liposomal B-EA6 formulation (Table 9) but not for liposomal B-B3 (Table 10). Surprisingly, the copolymer formulation of B-B3 was found to be superior for delivering the B-B3 to the lipoprotein fraction compared to the liposomal formulation (Table 9). Delivery of the B-EA6 was comparable to the liposomal formulation. The results also showed that delivery of both liposomal and copolymer formulation of EA6-B and B3-B to the lipoprotein fraction was more efficient than with DMSO formulations.

TABLE 9

Percent B-B3 associated with various plasma fractions following centrifugal separation

| Band | Plasma Component | Liposomal BPD-MA % (n = 4) | Liposomal B-B3 % (n = 2) | P123 B-B3 % (n = 6) | DMSO B-B3 % (n = 2) |
|---|---|---|---|---|---|
| A | Lipoprotein | 85.0 (3.6)[1] | 61.4 (1.76) | 91.8 (1.2) | 61.2 (1.12) |
| B' | Salt water | 5.8 (1.4) | 9.4 (0.42) | 4.6 (1.3) | 15.0 (0.21) |
| C' | Albumin | 6.5 (2.3) | 23 (1.51) | 0.8 (0.1) | 1.9 (0.65) |
| C | Other proteins | 0.6 (0.2) | 1.4 (0.01) | 0.4 (0.2) | 4.6 (0.23) |
| X | Pellet | 2.1 (0.8) | 4.8 (0.16) | 2.4 (0.2) | 17.4 (0.47) |
|  | Average Recovery | 79.75 | 95.55 | 103.03 | 76.1 |

[1]value in parenthesis is standard deviation

TABLE 10

Percent B-EA6 associated with various plasma fractions following centrifugal separation

| Band | Plasma Component | Liposomal BPD-MA % (n = 4) | Liposomal B-EA6 % (n = 2) | P123 B-EA6 % (n = 6) | DMSO B-EA6 % (n = 2) | DMSO BPD-MA % (n = 2) |
|---|---|---|---|---|---|---|
| A | Lipoprotein | 85.1 (2.8)[1] | 89.4 (0.04) | 91.4 (2.3) | 59.0 (1.44) | 74.0 (2.3) |
| B' | Salt water | 6.8 (1.0) | 8.5 (0.04) | 3.5 (1.3) | 14.6 (1.10) | 15.7 (1.8) |
| C' | Albumin | 6.9 (1.7) | 0.8 (0.10) | 1.5 (0.6) | 2.8 (0.04) | 6.0 (0.3) |
| C | Other proteins | 0.5 (0.2) | 0.4 (0.01) | 0.2 (0.2) | 2.6 (0.09) | 2.8 (0.4) |
| X | Pellet | 0.7 (0.4) | 0.9 (0.01) | 4.2 (1.8) | 21.0 (2.45) | 1.4 (0.5) |
|  | Average Recovery | 92.05 | 90.8 | 87.17 | 77.95 | 84.2 |

[1]value in parenthesis is standard deviation

Addition of BPD-MA/DMSO to plasma resulted in inefficient delivery to the lipoprotein fraction in comparison to the liposomal formulation. All drugs added to plasma in DMSO resulted in high drug concentration in the salt/water fraction and in the pellet. Although there appears to be a genuine binding to the sedimented flocculent, drug aggregates also end up in the pellet. Low total drug recoveries were observed in DMSO formulations, which probably reflects inadequate dissociation of these aggregates in the detergent system used to read assays.

The above example demonstrates that the copolymer formulations of B-ring compounds are either comparable or superior to the liposomal formulations for the delivery of the drug to the lipoprotein fraction of the plasma. This is important for PDT because most target tissues, those undergoing rapid proliferation or repair, express high levels of LDL receptors, and lipoprotein mediated delivery results in selective accumulation of photosensitizers in these tissues.

Example 10

Cellular Uptake of Liposomal and Polymer Delivery of Photosensitizers

The following example illustrates the efficiency of cellular uptake using block copolymer formulation of a B-ring photosensitizer, B-B3, in comparison with the standard liposomal formulation of BPD-MA.

For this experiment the B-B3 copolymeric formulation and the BPD-MA liposomal formulation were prepared as described in Examples 5 and 6, respectively. The protocol for setting up the cell cultures and conditions for the cellular assay essentially followed Richter et al. (*Proc. SPIE*, 2078: 293-304, September 1993). L1210 cells in DMEM and 10% FBS (single experiment, 3 sets) were incubated with the formulations at a concentration of 3 μg/ml and examined for uptake in the cells over time. Cells were recovered by centrifugation, the pellet briefly rinsed, and the cells lysed by freeze thawing in the presence of 2% Triton X-100®. An equal volume of methanol was added and fluorescence was read at 694 nm ($\lambda_{ex}$ 440 nm).

FIG. 1 shows that cellular uptake of the B-B3 copolymer formulation was very rapid compared to BPD-MA liposomal formulation. 50% uptake level was observed to be close to 'zero' incubation time, with uptake of B-B3 peaking at around 20 min. In comparison, BPD-MA achieved saturation level at 30 min, with 50% uptake at approximately 5 min. It appears that the permeability of cellular membranes to B-B3 is higher in the presence of P123. This is important for the effective penetration of the photosensitizer into the PDT sensitive sites in the intracellular infra structure.

These results suggests that light exposure for PDT treatment in general could be applied as early as 10 to 15 min post injection if the photosensitizer is formulated in copolymers.

The above example demonstrates rapid uptake of a B-Ring photosensitizer by cells when using copolymer. Further because of the rapidity of the photosensitizer uptake using copolymer formulation by the targeted cells, the irradiation step for PDT can be carried out earlier than previously reported for liposomal or other formulations.

Example 11

Comparison of Block Copolymer and Liposomal Photosensitizer Formulations: in vitro Phototoxicity The following example illustrates the advantages of using Pluronic based formulations for effective delivery of B-ring photosensitizer drugs to the cells in a model system.

In this experiment copolymer P123, liposomal and DMSO formulations of the B-ring compounds, B-EA6 and B-B3, were examined for their in vitro cytotoxicity effects. Exposure to drugs was carried out in the presence and absence of fetal calf serum (FCS) as a model to study transfer of drug to cells in vivo. BPD-MA liposomal formulation was used as the standard and the DMSO formulation as the control. The DMSO, Pluronic micellar and liposomal formulations of the photosensitizers were prepared as described in Example 9. A suspension of L1210 cells was prepared and exposed to various drug formulations (drug concentrations ranging from 0-50 ng/ml) either in the absence or presence of 10% fetal calf serum (FCS). One hour later, the drug was removed by pelleting the cells by centrifugation. The pellet was briefly washed with 1 ml DME and resuspended in 5% FCS/DME. 100 μl of the cell suspension was aliquoted into 6 wells of a 96 well plate, and the plate exposed to light at 10 J/cm$^2$. Viability was determined 24 h post exposure using the MTT assay (Mosmann, *J. Immunol. Meth.* 65:55-63, 1983).

TABLE 11

| Photosensitizer | Carrier | $LD_{50}$ (ng/ml) | |
| --- | --- | --- | --- |
| | | −FCS | +FCS |
| BPD-MA | Liposomal | 4.0 | 38.0 |
| B-B3 | Copolymer | 0.68* | 16.6* |
| B-B3 | Liposomal | 3.0 | 30.0 |
| B-B3 | DMSO | 7.2 | 37.0 |
| B-EA6 | Copolymer | 2.06* | 12.9* |
| B-EA6 | Liposomal | 4.7 | 19.7 |
| B-EA6 | DMSO | 4.7 | 20.0 |

Table 11 shows the $LD_{50}$ values determined for in vitro photocytotoxicity for formulations of B-ring drugs in block copolymers compared to drug delivery using liposomes and solutions in DMSO.

The presence of FCS better represents in vivo conditions for cellular exposure to systemic drugs, and under these conditions it generally competes with the cells for drug binding. However, under both conditions, it is clear from the $LD_{50}$ values that formulations of B-ring drugs in Pluronic have greater potency than liposomal formulations or solutions in DMSO. This indicates superior delivery of drug in a non-aggregated form to cells or plasma proteins. Without being bound by theory, the advantage could also be partly attributed to permeabilization of cellular membranes by poloxamers, which would allow better access of the drug to PDT-sensitive intracellular sites.

The above example demonstrates that the B-ring compounds formulated with P123 were successfully delivered to the cells in a non-aggregated form. The delivery of the photosensitizer drug with the copolymer formulation was found to be superior to the liposomal formulations.

Example 12

Comparison of B-B3 Copolymer and Liposomal Formulations for PDT Treatment of Arthritis in MRL/lpr Mouse Model Arthritis in the MRL/lpr mouse strain was enhanced by giving 2 intradermal injections (thoracic and inguinal sites) with 0.05 ml of complete Freunds adjuvant containing 10 mg/ml heat-inactivated *M. tuberculosis*. PDT was given on days 0, 10 and 20 following CFA treatment. PDT was carried out as follows; 3 groups of MRL/lpr mice were injected intravenously with B-B3 at 0.5 mg/kg (copolymer or liposomal formulations), after which they were protected from light. The third group was injected with copolymer alone at an equivalent copolymer concentration to that found in the formulation. An hour later, they were exposed to light at 80 J/cm$^2$ for 1.5 h (8 mW/cm$^2$).

Figure 2:
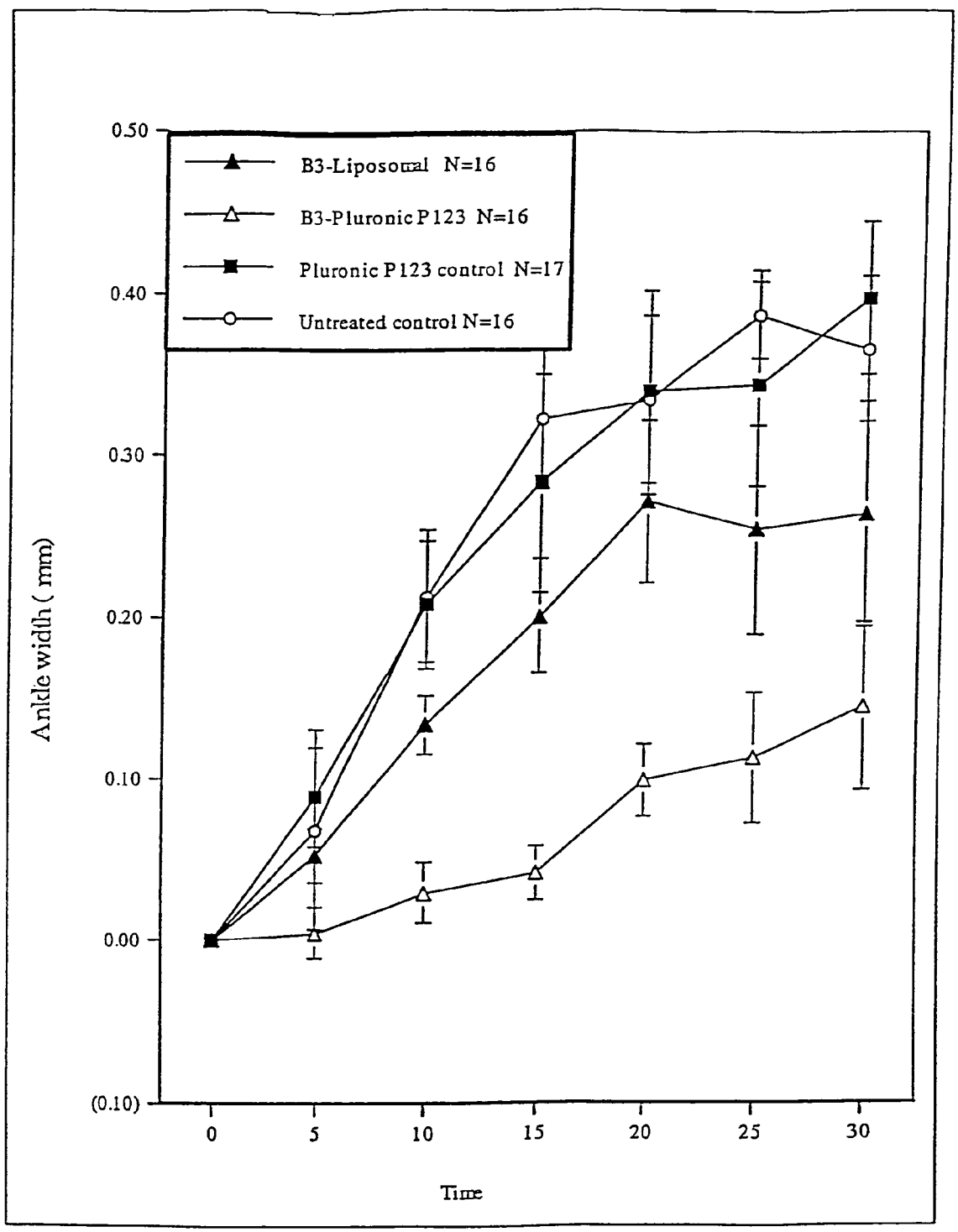
FIG. 2 compares the effectiveness of liposomal and copolymer formulations of B-B3 in controlling joint inflammation in the MRL-lpr mouse model using transcutaneous PDT. Mice receiving copolymer alone exhibited arthritic symptoms similar to the untreated control. The liposomal formulation of photosensitizer B-B3 showed improved suppression of the inflammation compared to controls in the early stages. Relative to the controls and the liposomal formulation, the B-B3 copolymer formulation was highly effective in controlling the inflammation as determined by the increase in ankle swelling.

Ankle width measurements were taken every 5 days prior to PDT treatment. The results of the above experiment are shown in FIG. 2. Mice receiving copolymer alone exhibited symptoms similar to the untreated control. The liposomal formulation of B-B3 in earlier part of the study showed better suppression of the inflammation compared to the controls. However, after day 25 there was an exacerbation of the inflammatory condition. Relative to the controls and the liposomal formulation, the B-B3 copolymer formulation was highly effective in controlling the inflammation as determined by increase in ankle swelling.

The above example demonstrates that copolymer formulation of B-B3 is superior to the liposomal formula for controlling an inflammatory disease in vivo in arthritic mouse model.

Example 13

Optimization of B-B3 Intravenous Formulation in Pluronic P123

The following example illustrates the effects of copolymer:drug ratio in achieving total drug incorporation.

Using formulation methods described in Example 5, the aim was to incorporate 2 mg/ml of B-B3 into 10% w/v P123. It was shown by this method that the B-B3 can typically be incorporated at ~1.8 mg/ml drug (based on absorbance readings and a molar extinction coefficient of 30425) 24 h post-hydration. This translates to approximately 10% drug loss. Unincorporated drug undergoes aggregation in aqueous solutions, and is characterized by the appearance of a 730 nm absorbance peak. Although the formulations can be made completely aggregate free by centrifugation or sterile filtration through 0.2 μm filters, this adds another step in the manufacturing process, which can be avoided by increasing the copolymer:drug ratio. A final drug concentration of 1 mg/ml resulted in complete incorporation of all added drug.

Example 14

Blending of Copolymers for Intravenous Formulations of B-B3

To achieve a solid final product, the hydrated material is lyophilized. Alternative means of drying include, but is not limited to, spray or freeze drying. It is important to determine whether the drying process affects the product integrity and to ascertain that formulation characteristics are retained on reconstitution.

In this experiment a 10% P123 (w/v) resulted in a thin film, with an oily appearance, which was difficult to hydrate. Counteracting the oily nature of P123 could be achieved by incorporation of copolymer that is in solid form at room temperature. The use of 1% w/w F127 with 9% w/v P123 instead of 10% P123 (w/v) produced a thin film, which was more readily hydrated. This composition was equally stable and was readily reconstituted following lyophilization. The use of blends may be used to tailor a formulation according to the needs of the particular drug substance and/or to compensate for properties lacking in a primary copolymer.

pH studies showed that acidification of B-B3 formulations was detrimental to formulation stability. This necessitates hydration of the solid drug-polymer with a very mild buffer to counteract acidification which occurs upon use of sterile packed distilled water as commonly practiced in clinical settings. Behavior of poloxamers is unaffected by pH, and the use of buffers would be entirely dependent on ionizable groups present on the drug substance. For example, B-EA6 does not display any pH-dependency.

The above example demonstrates that using blend of copolymers for formulating photosensitizer improved the rehydration of the photosensitizer after lyophilization. It also shows that only mild buffers are needed since the copolymer is unaffected by pH, unlike liposomes.

Example 15

Deposition of Block Copolymer Photosensitizer Based Formulations on Sugar Crystals This example demonstrates that the use of the micro thin film can be extended beyond lipids to any alternative carriers for hydrophobic photosensitizer drugs. The use of the micro-thin film technique for formulation of photosensitizer drug using block copolymer and deposition on sugar crystals resulted in a solid-state formulation that is easy to hydrate.

In this experiment the deposition of the photosensitizer BPD-MA with the block copolymer Pluronic® F127 onto the sugar lactose was examined. Formulations containing 5% (w/v) and a 10% (w/v) F127 were tested. 0.5 g lactose and 10 mg BPD-MA were added to two rotary evaporation flasks. A stock solution of 0.2 mg/ml F127 was prepared in $CH_2Cl_2$. 1.25 ml (for 5% w/v) and 2.5 ml (for 10% w/v) F127 stock solution was added to each flask. The final volume in each flask was made up to 5.0 ml with $CH_2Cl_2$ and the components mixed to ensure complete dissolution. The solvent was removed by rotary evacuation at 50° C., and the flask left under vacuum for a further 15 min at 23° C. Micro-thin film deposits were scraped from the walls and hydrated in 5 ml water at 50° C. The formulations were filtered twice using 0.2 µm syringe filters (Acrodisc, polysulphone).

It was observed that both the thin film formulations dissolved easily, particularly 5% w/v, which went into solution immediately on addition of water. Both the formulations (5% w/v and 10% w/v F127) filtered easily through 0.2 µm filters and with no drug loss.

The above example demonstrates that solid-state formulation of an A-ring photosensitizer and block copolymer carrier deposited on sugar crystals offers a very simple alternative to liposomal-based formulations. Furthermore, if prepared under sterile GMP conditions it can provide a simple, one step manufacturing process.

Example 16

Deposition of Block Copolymer Photosensitizer Based Formulations onto Sugar Crystals Using Ethanol as Solvent This experiment examines the substitution of ethanol for $CH_2Cl_2$ as the solvent for dissolving the block copolymer F127, and photosensitizer BPD-MA, for deposition on lactose crystals. It also examined the use of lower concentration of F127 for the formulation.

The experimental conditions and components were the same as Example 15 with the exception of the following changes. A stock of 0.2 mg/ml F127 was prepared in ethanol and 0.65 ml (2.5% w/v) and 1.25 ml (5% w/v) of the stock solution was added to two flasks. The final volume was made up to 5.0 ml with ethanol and the contents dissolved with warming. Ethanol was removed by rotary evacuation at 50° C., left under vacuum for 15 min at room. Micro-thin film deposits were scraped from the walls and dissolved in 5 ml water at 50° C. as previously described. Samples were filtered 3 times through 0.2 µm syringe filters.

Substitution of ethanol for $CH_2Cl_2$ as the solvent for dissolving and depositing the formulation on lactose crystals was successful. Both the 2.5% and 5% w/v of F127 formed micro-thin films after removal of ethanol, and were easily hydrated. Further these formulations were filtered through 0.2 µm filter with no resistance.

The above example demonstrates that ethanol can replace $CH_2Cl_2$ as the volatile solvent for dissolving block copolymer and A-ring photosensitizer for deposition on lactose sugar crystals.

Example 17

B-ring Photosensitizers Formulations Using Mixed Block Copolymers

This example illustrates the of blended block copolymers for dissolving and improving the hydration of B-ring photosensitizer solid support based formulations.

The poloxamer that was found to be useful in formulating a range of tetrapyrrolic drugs was Pluronic® P123, under the above conditions.

In this experiment formulation of B-ring photosensitizer, B-B3 at 2 mg/ml with blended P123 and F127 or PVP, using the thin film method as described in Example 15 were examined. The aim of the following experiment was to determine whether incorporation of solid compounds (e.g., PVP, F127) into the formulation might help to counteract the waxy nature of P123 in the thin film, hence improving hydration characteristics without destabilizing the formulation.

The polymer combinations used in this experiment are described in the following table. The relative ease of thin film hydration for each combination was observed. The drug concentration retention was determined by absorbance at t=0, 3 h and 24 h. Following centrifugation each sample was diluted to 1:100 dilution in MeOH and A690 measured.

The relative ease of hydration for the poloxamer or poloxamer combinations was observed to be as follows:
5% P123+5% F127>5% P123+5% PVP>10% P123+5% PVP>10% P123

P123 is semi solid and its waxy in nature makes it very difficult to hydrate. Based on the above results, formulations with a lower P123 content hydrated more readily. The presence of solid compounds such as PVP and F127 in combination with P123 facilitated the hydration of the formulations. Incorporation of crystalline lactose is advantageous because it resulted in the improvement of the quality of the thin film, which was drier and thinner and therefore easier to hydrate, compared to the previous poloxamer based thin films, which were then hydrated with iso-osmolar lactose solution.

The result of the drug retention measurement over time is shown in Table 12.

TABLE 12

B-B3 Retention In Various Polymeric Formulation Determined By Absorbance Readings (690 nm)

| Polymer Combination | $A_{690}$ | | |
|---|---|---|---|
| | T = 0 | T = 3 h | T = 24 h |
| 5% P123 + 5% F127 | 0.88 | 0.54 | 0.42 |
| | 0.93 | 0.57 | 0.45 |
| 5% P123 + 5% PVP | 0.84 | 0.75 | 0.57 |
| | 0.91 | 0.75 | 0.61 |
| 10% P123 + 5% PVP | 0.88 | 0.69 | 0.45 |
| | 0.89 | 0.71 | 0.44 |
| 10% P123 | 0.77 | 0.91 | 0.84 |
| | 0.81 | 0.91 | 0.79 |

The results show that all samples formulated in blended polymers lose drug on standing over 24 hours. It was observed that 10% P123 retained the most drug. The drug retention in the formulation after 24 h was in the following order:

10% P123>10% P123+5% PVP>5% P123+5% PVP>5% P123+5% F127

These results indicate that the presence of P123 in the formulation allows for B-EA6 drug to be stable in the formulation. It has been previously shown that drug formulation with 10% w/v F127 resulted in poor formulation efficiency for B-EA6 (see Example 4 above). The use of various molecular weights of PVPs with the photosensitizer BPD-MA, also resulted in poor retention of the drug (results not shown).

The above example demonstrates that B-ring photosensitizer drug formulation and hydration is improved with blending of polymers and use of lactose. Pluronic P123, a block copolymer that is semi-solid and waxy at ambient temperatures, when blended with PVP or other block copolymers, such as Pluronic F127, which are solids, was shown to improves hydration of B-EA6 thin film preparation.

Example 18

Photosensitizers Formulations Using Mixed Block Copolymers and Dissolvable Crystalline Solid Support The objective of this experiment was to optimize the photosensitizer drug stability using different blends of copolymer content in the formulation while retaining the ease of hydration of the sugar based thin film. The effect of lyophilization of hydrated material was also examined.

Initially the aim was to incorporate 2 mg/ml of B-B3 into 10% w/v P123 by this method. It was shown in previous work that ~1.8 mg/ml B-B3 can typically be retained 24 h post-hydration. This translates to approximately 10% drug loss. Unincorporated B-ring drugs undergo aggregation in aqueous solutions, which is characterized by appearance of a 730 nm absorbance peak. Although the formulations can be made completely aggregate free by centrifugation or sterile filtration through 0.2 μm filters, this adds another step in the manufacturing process, which can be avoided by increasing the copolymer:drug ratio.

In this experiment the B3-B was formulated using the sugar trehalose (9.5% w/v) to give a final drug concentration of 1 mg/mL. The non-blended and blended poloxamer contents of the test samples were as follows: 7.5% w/v P123; 9% w/v P123+1% w/v F127; and 10% w/v P123.

B-B3 was dissolved in $CH_2Cl_2$ to a concentration of 1 mg/mL, and 1 mL of the solution was dispensed into 25 ml round bottom flasks. A 100 mg/mL stock solution of Pluronic P123 in $CH_2Cl_2$ was prepared, and dispensed into the flasks, followed by solid F127 to give 7.5% w/v P123; 9% w/v P123+1% w/v F127; and 10% w/v P123, in duplicate. Trehalose was added to give 9.5% w/v final concentration in each of the flasks. Solvent was removed by rotary evaporation to give a micro-thin film composed of B3-B and copolymers deposited on trehalose crystals. The films were hydrated with distilled water (adjusted to pH 7.6) at room temperature. Hydrated samples were studied for stability at room temperature for up to 24 h by spectroscopic scanning between 650 and 750 nm following 1:100 dilution in water, pH 7.6. After 24 h stability studies, samples were lyophilized at −10° C.

The relative ease of reconstitution of the lyophilized formulations of the B-B3 with the various poloxamer combinations deposited on trehalose was observed to be as follows: 7.5% P123>9% P123+1% F127>10% P123

TABLE 13

Dependence of formulation stability on block copolymer content

|  | Lyophilized Formulation $A_{690}$ Post Reconstitution (4 h) |
|---|---|
| 7.5% P123 | 0.308 |
|  | 0.299 |
| 1% F127 + 9% P123 | 0.332 |
|  | 0.382 |
| 10% P123 | 0.351 |
|  | 0.342 |

These results once again suggests that the lower the content of the waxy copolymer (e.g. Pluronic P123), the greater the ease of hydration. In the previous example (Example 17) addition of 5% w/v solid copolymer (F127) into P123 was shown to cause destabilization of the formulation, however in the present experiment incorporation of 1% w/v resulted in superior hydration of the micro-thin film, without compromising formulation (Table 13).

The above example demonstrates that photosensitizers using blended poloxamers as carriers and depositing onto sugar results in stable solid-state formulations that are easier to hydrate, and retain the photosensitizer drug in a non-aggregated form.

Example 19

Photosensitizers Formulations Using Mixed Block Copolymers and Soluble Crystalline Solid Supports The following example demonstrates that complexes of photosensitizer drug blended copolymers P123 and F127 (lyophilized material) hydrate easier if trehalose is used as a solid support instead of lactose.

This experiment examined the use of blended block copolymers, 9% P123 and 1% F127 with 9.5% w/v lactose or trehalose, as solid supports for formulating 1 mg/ml B-B3. The control was 10% P123 with either 9.5% w/v lactose or trehalose. The procedure was carried out as described in Example 18 and the hydration of the thin film, or ease of reconstitution of the lyophilized preparations were examined. Formulations of B-B3 (1 mg/mL) with copolymer content of 10% P123 and 9% P123+1% F127 were prepared for comparison. Thin films were hydrated with 0.01M citrate-phosphate buffer pH 7.4. 1 mL of hydrated formulations was aliquoted into 2 mL lyophilization vials and lyophilized.

All the samples formed lyophilized cakes that were observed to be fluffy and uniform in appearance. The ease of hydration of lyophilized cakes were as follows:
9% P123+1% F127+trehalose>10% P123+trehalose>9% P123+1% F127+lactose>10% P123+lactose Although all B-B3 formulation samples formed cakes upon lyophilization, formulations containing trehalose were relatively easier to reconstitute compared to lactose based formulations. This was irrespective of copolymer content. It was also confirmed that addition of solid copolymer, F127 to a concentration of 1% w/v resulted in easier reconstitution of the lyophilized cakes for both trehalose and lactose containing formulations.

Example 20

Comparison of Tumor Recurrence in Mice Model Treated with PDT Using A- & B-ring Photosensitizers in Block Copolymer and Liposomal Formulations The following example illustrates that the efficiency of poloxamer based photosensitizer formulations over liposomal formulation in a tumor mouse model following PDT.

Photosensitizer formulations were prepared in 10% w/v Pluronics as described in Example 4. BPD-MA was formulated in F127. B-ring compounds B-EA6 and B-B3, were prepared in P123 due to insufficient drug loading in F127. Liposomal BPD-MA formulation was Verteporfin™ and B-ring compounds were formulated in the same lipid composition. Where DMSO/plasma preparations were made, the DMSO dissolved drug was added directly to mouse plasma and the drug association with different plasma components was observed.

In these experiments the tumor model used was the DBA/2 mouse (males) inoculated intradermally with M1 rhabdomyosarcoma tumor cells (M1, ATCC). When tumors reached a diameter of 4-6 mm, the mice (n=10, unless otherwise stated) were treated with photodynamic therapy (PDT). PDT involved intravenous injection of the formulated drug in 0.2 mL volume of PBS. This was followed by exposure of the tumor region to laser light (Argon pumped dye laser (5W), 690 nm, 50 J/cm$^2$) 15 min later. Animals were then monitored for tumor recurrence over a 20 day period post treatment.

TABLE 14

Results of Tumor Cure Following Administration of Poloxamer Formulations; Comparison to Liposomal BPD-MA

| Photosensitizer/ Formulation Type | Photosensitizer Dosage | Percent (%) Mice Tumor Free | | |
|---|---|---|---|---|
| | | Day 7 | Day 14 | Day 20 |
| BPD-MA | | | | |
| Liposomal | 1.0 mg/kg | 100 | 100 | 30 |
| Pluronic F127 | 1.0 mg/kg | 100 | 60 | 60 |
| B-EA6 | | | | |
| Liposomal | 1.0 mg/kg | 90 | 70 | 60 |
| Pluronic P123 | 1.0 mg/kg | PT[1] | PT[1] | PT[1] |
| Pluronic P123 | 0.5 mg/kg | 80 | 60 | 40 |
| B-B3 | | | | |
| Liposomal | 1.0 mg/kg | 0[2] | —[2] | —[2] |
| Pluronic P123 | 1.0 mg/kg | 100 | 80 | 60 |
| Pluronic P123 | 1.2 mg/kg | 100[3] | 67[3] | 67[3] |
| Pluronic P123 | 1.25 mg/kg | 100 | 100 | 80 |

[1]Mice suffered from phototoxic (PT) reaction at the site of light exposure and were subsequently euthanized.
[2]n = 5, zero tumor cure, mice euthanized at day 7
[3]n = 3

Table 14 summarizes the result of the above experiments. The performance of B-ring compounds was compared to the liposomal BPD-MA (Verteporfin) formulation which was used as the standard for assessing performance of other photosensitizers and formulations. It was observed that at the end of the 20 day period, mice treated with the poloxamer formulation were twice as likely to remain tumor free compared to those treated with liposomal BPD-MA.

Although B-EA6 formulated poorly in liposomes (in terms of drug loading), it demonstrated the greatest potency of the three liposomal drugs tested in the mouse tumor model. Administration of the 1 mg/kg B-EA6, formulated in P123, to tumor bearing mice resulted in a strong phototoxic reaction (edema) at the irradiated site, and the animals were consequently euthanized. This observation suggested that better drug delivery is achieved using poloxamers compared to the liposomal formulations at the same drug dosage. At a lower dose of 0.5 mg/kg, a cure rate was achieved similar to that of liposomal formulations of B-EA6 and BPD-MA at 1 mg/kg.

B-B3 demonstrated greatest sensitivity to the drug delivery agent (or "carrier") used in the formulation. At these levels, the plasma/DMSO preparation was found to be completely ineffective for PDT purposes. One of the most important modes of action of PDT is the disruption of neovasculature. Performance of B-B3 formulated in P123 at 1 mg/ml was marginally better than that of liposomal BPD-MA, and comparable to BPD-MA in poloxamer formulations. Increasing the dose B-B3 by 25% resulted in a marked improvement in performance in the tumor assay.

The results show that B-ring compounds formulated in poloxamers such Pluronic P123 enhanced performance of PDT in vivo. Without being bound by theory, the observed effects could be attributed partly to facilitation of the drugs across cellular membranes by the poloxamer and partly to improved delivery of drug to plasma lipoproteins. Although both B-ring compounds EA6 and B-3 had a tendency to aggregate, it was the amount associated with the lipoprotein fraction that dictated the efficacy of PDT in vivo. B-B3 showed poor delivery to the lipoprotein fraction for both liposomal and DMSO/plasma formulations (Table 9) and this resulted in failure of PDT in the tumor model. On the other hand, in the case of liposomal and Pluronic formulation of B-EA6, delivery to lipoproteins was equivalent (Table 10), the results in vivo were not markedly different.

Furthermore, when comparing liposomal and poloxamer formulations of B ring compounds, a lower concentration of the photosensitizer in the poloxamer formulations appears to give similar results to those in the liposomal preparations. In fact, excessive photosensitivity at the irradiated site when using B-EA6 at the dose traditionally used for liposomal BPD-MA suggests that the drug dosage for achieving good PDT response can be considerably lowered. The above example demonstrates that block copolymers allow formulation and potential use of B-ring compounds (which were found ineffective or difficult to formulate in liposomes or homopolymers) to give photosensitizer products with greatly enhanced drug delivery characteristics.

All references cited herein, including patents, patent applications, and publications, are hereby incorporated by reference in their entireties, whether previously specifically incorporated or not. As used herein, the terms "a", "an", and "any" are each intended to include both the singular and plural forms.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

We claim:

1. A pharmaceutical composition comprising:
   (a) a complex formed from one or more photosensitizer drugs; one or more block copolymer in liquid form, wherein said copolymer is i) not an amphiphilic polymer of polystyrene sodium sulphonate and vinyl naphthalene, and ii) not poloxamer 188; and
   (b) a pharmaceutically acceptable excipient;
   wherein said complex is selected from the group consisting of micelles, emulsions, gels and matrices; and
   wherein said block copolymer comprises polyoxyethylene and polyoxypropylene, wherein said polyoxyethylene-polyoxypropylene block copolymer is selected from the group consisting of poloxamer 403 (P 123), poloxamer 407 (FI27), poloxamer 402 (LI22), poloxamer 181 (L61), poloxamer 401 (LI21), poloxamer 185 (P65), and poloxamer 338 (FI08).

2. The composition of claim 1, wherein said complex is selected from the group consisting of micelles, emulsions and matrices.

3. The composition of claim 1, wherein said photosensitizer is selected from the group consisting of porphyrins and porphyrin derivatives, pyrroles, tetrapyrrolic compounds, and expanded pyrrolic macrocycles wherein said porphyrin derivatives are selected from the group consisting of green porphyrins, tetrahydrochlorins, pyropheophorbides, purpurins, texaphyrins, phenothiaziniums, phthalocyanines, naphthalocyanines, porphycenes and pheophorbides.

4. The composition of claim 3, wherein said tetrahydrochlorins are selected from the group consisting of chlorins, hydroxychlorins, bacteriochlorins, and isobacteriochlorins.

5. The composition of claim 3, wherein said green porphyrin is a benzoporphyrin derivative (BPD).

6. The composition of claim 5, wherein said BPD is selected from the group consisting of BPD-MA, BPD-MB, A-EA6, B-EA6, A-B3 and B-B3.

7. A method for formulating the pharmaceutical composition according to claim 1 comprising combining one or more photosensitizer and one or more block copolymer wherein said copolymer is in a liquefied state, said photosensitizer is soluble in said copolymer, and said copolymer is i) not an amphiphilic polymer of polystyrene sodium sulphonate and vinyl naphthalene, and ii) not poloxamer 188.

8. A method for conducting photodynamic therapy comprising:
   (a) administering a photosensitizer and copolymer complex produced by hydration of the pharmaceutical composition of claim 1 to a subject in need of photodynamic therapy; and
   (b) irradiating said subject to activate said photosensitizer; wherein said copolymer is i) not an amphiphilic polymer of polystyrene sodium sulphonate and vinyl naphthalene, and ii) not poloxamer 188.

9. A method for formulating the pharmaceutical composition of claim 1 comprising combining one or more photosensitizer and one or more block copolymer in solution, wherein said copolymer is i) not an amphiphilic polymer of polystyrene sodium sulphonate and vinyl naphthalene, and ii) not poloxamer 188.

10. The method of claim 9 further comprising the step of optionally drying said photosensitizer and copolymer combination.

11. The method of claim 10 further comprising the step of optionally hydrating said photosensitizer and copolymer combination to form a complex.

12. The method of claim 11 wherein said combining step further comprises a hydratable solid support on which said photosensitizer and block copolymer combination may deposit.

13. The method of claim 12, wherein said solid support is not capable of dissolving in said liquefied copolymer.

14. The method of claim 12, wherein said solid support is capable of dissolving in said optional hydrating step.

* * * * *